US010011619B2

(12) United States Patent
Dyballa et al.

(10) Patent No.: US 10,011,619 B2
(45) Date of Patent: *Jul. 3, 2018

(54) PROCESS FOR REDUCING THE CHLORINE CONTENT OF ORGANOTETRAPHOSPHITES

(71) Applicant: EVONIK DEGUSSA GMBH, Essen (DE)

(72) Inventors: Katrin Marie Dyballa, Recklinghausen (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/363,746

(22) Filed: Nov. 29, 2016

(65) Prior Publication Data
US 2017/0158719 A1 Jun. 8, 2017

(30) Foreign Application Priority Data

Dec. 3, 2015 (EP) .................................... 15197762

(51) Int. Cl.
C07F 9/02 (2006.01)
C07F 9/06 (2006.01)
C07F 9/655 (2006.01)
C07F 9/576 (2006.01)
C07F 9/6574 (2006.01)
C07F 9/6584 (2006.01)
C07F 9/145 (2006.01)
C07F 9/24 (2006.01)

(52) U.S. Cl.
CPC .............. C07F 9/062 (2013.01); C07F 9/145 (2013.01); C07F 9/2475 (2013.01); C07F 9/5765 (2013.01); C07F 9/65746 (2013.01); C07F 9/65848 (2013.01)

(58) Field of Classification Search
CPC .............. C07F 9/02; C07F 9/06; C07F 9/655
USPC ............................................. 558/78; 546/22
See application file for complete search history.

(56) References Cited

U.S. PATENT DOCUMENTS

| 3,980,739 | A | 9/1976 | Frey | |
| 4,835,299 | A | 5/1989 | Maher et al. | |
| 9,701,697 | B2* | 7/2017 | Dyballa | C07F 9/025 |
| 2008/0076944 | A1 | 3/2008 | Bartsch et al. | |
| 2013/0317246 | A1 | 11/2013 | Kreidler et al. | |

FOREIGN PATENT DOCUMENTS

| DE | 10 2004 049 339 A1 | 4/2006 |
| DE | 10 2011 002 640 A1 | 7/2012 |
| DE | 10 2014 206 520 A1 | 11/2014 |
| EP | 0 285 136 A2 | 10/1988 |
| WO | 2013/098368 A1 | 7/2013 |
| WO | 2014/177355 A1 | 11/2014 |
| WO | 2015/121007 A1 | 8/2015 |
| WO | 2015/176927 A1 | 11/2015 |

OTHER PUBLICATIONS

International Search Report for EP15197762 dated Feb. 10, 2016 (1page).
Franke, R., Selent, D., and Borner, A. Applied Hydroformylation. American Chemical Society, ACS Publications, Chemical Reviews, 2012. 5675-5732.
Armarego, Wilfred L.F., et al. Purification of Laboratory Chemicals, Butterworth Heinemann (Elsevier), 6th edition, Oxford 2009 (index and chapter abstracts provided).
Harris, Robin K. et al. NMR Nomenclature, Nuclear Spin Properties and Conventions for Chemical Shifts. Pure Appl. Chem., 2001, 73, pp. 1795-1818.
Harris, Robin K. et al. Further Conventions for NMR Shielding and Chemical Shifts. Pure Appl. Chem., 2008, 80, pp. 59-84.
B. Cornils, W. A. Herrmann, Applied Homogeneous Catalysis with Organometallic Compounds, vol. 1 & 2, VCH, Weinheim, New York, 1996. Forward, Preface and Table of Contents provided.
Phosphorus(III) Ligands in Homogeneous Catalysis—Design and Synthesis by Paul C. J. Kamer and Piet W. N. M. van Leeuwen; John Wiley and Sons, 2012. Table of Contents provided.
cf. Merkblatt 893 "Edelstahl rostfrei für die Wasserwirtschaft" [Information Sheet 893 "Corrosion-Free Stainless Steel for Water Management"], 1st edition 2007, publisher: Informationsstelle Edelstahl Rostfrei, Diisseldorf. pp. 1-17.
DIN 51408. Testing of Liquid mineral oil hydrocarbons; determination of chlorine content; Wickbold's combustion method. Jun. 1983. 4 pages.
DIN51408-2. Testing of mineral oil hydrocarbons—Determination of chlorine content—Part 2: Microcoulometric determination, oxidation method. Jun. 2009. 10 pages.
DIN EN ISO 10304-1. Water Quality of dissolved anions by liquid chromatography of ions—Part1: Determination of bromide, chloride, fluoride, nitrate, nitrite, phosphate and sulfate. Jul. 2009. 23 pages.
DIN EN ISO 10304-3. Determination of dissolved anions by liquid chromatography of ions—Part 3: Determination of chromate, iodide, sulfite, thiocyanate and thiosulfate. Nov. 1997. 32 pages.
DIN EN ISO 10304-4. Determination of dissolved anions by liquid chromatography of ions—Part 4: Determination of chlorate, chloride and chlorite in water with low contamination. Jul. 1999. 26 pages.
Taiwanese Search Report dated Dec. 3, 2017 for Taiwanese Patent Application No. 105139501 (1 page).

* cited by examiner

Primary Examiner — Charanjit Aulakh
(74) Attorney, Agent, or Firm — Smith, Gambrell & Russell, LLP

(57) ABSTRACT

Universally usable process for reducing the chlorine content of organotetraphosphites.

14 Claims, No Drawings

PROCESS FOR REDUCING THE CHLORINE CONTENT OF ORGANOTETRAPHOSPHITES

The invention relates to a universally usable process for reducing the chlorine content of organotetraphosphites.

Organophosphorus compounds have gained considerable industrial significance because of their wide range of use. They are used directly as plasticizers, flame retardants, UV stabilizers or as antioxidants. In addition, they are important intermediates in the production of fungicides, herbicides, insecticides and pharmaceuticals.

A specific field of use of the organophosphorus compounds is catalysis:

For instance, especially phosphines, phosphites and phosphoramidites are used as ligands in catalyst complexes, which are used in turn for the homogeneous catalysis of processes operated on an industrial scale. Particular mention should be made of the hydroformylation of unsaturated compounds with carbon monoxide and hydrogen, which generally takes place in the presence of a homogeneous catalyst system which has a metal and at least one organophosphorus compound as ligand.

An introduction into homogeneously catalysed hydroformylation is given by: B. CORNILS, W. A. HERRMANN, Applied Homogeneous Catalysis with Organometallic Compounds, vol. 1 & 2, VCH, Weinheim, N.Y., 1996; R. Franke, D. Selent, A. Börner, Applied Hydroformylation, Chem. Rev., 2012, DOI:10.1021/cr3001803.

The synthesis of phosphorus ligands is described repeatedly in the literature. A good overview can be found in: "Phosphorus(III) Ligands in Homogeneous Catalysis—Design and Synthesis" by Paul C. J. Kamer and Piet W. N. M. van Leeuwen; John Wiley and Sons, 2012.

In the synthesis of these ligands, chlorine-containing reagents are frequently used. For instance, in the synthesis of phosphite ligands, phosphorus trichloride ($PCl_3$) is usually used. The chlorine compounds used in the preparation of organophosphorus compounds present many difficulties in the proper use or further processing of the organophosphorus compound:

For instance, the desired organophosphorus compound is never obtained in pure form immediately, and is always obtained in contaminated form as an organophosphorus product which, as well as the desired organophosphorus compound, also contains contaminants. The contaminants are unconverted or incompletely converted reagents, auxiliaries or products from side reactions. In this context, contaminants in the form of chlorine compounds present particular difficulties:

If the chlorine-containing contaminants get into a steel pressure reactor together with the organophosphorus compound used as ligand, the pressure reactor is subject to increased corrosion as a result of the chloride. This is especially true of continuous processes, in which the organophosphorus compound is metered in over the course of the reaction. This is the case, for example, when the organophosphorus compound is used as a ligand in industrial scale hydroformylation. The metered addition inevitably also results in an accumulation of the secondary components in the reactor. This is critical especially when chloride is one of the secondary components, since chloride attacks even stainless steels (cf. Merkblatt 893 "Edelstahl rostfrei für die Wasserwirtschaft" [Information Sheet 893 "Corrosion-Free Stainless Steel for Water Management"], 1st edition 2007, publisher: Informationsstelle Edelstahl Rostfrei, Düsseldorf.)

In the presence of chloride ions, there is a particular risk of stress-cracking corrosion, which can lead in more favourable cases to a premature shutdown of the process and to a reactor overhaul, but in less favourable cases even to rupture of the reactor. It is therefore of overriding importance to prevent entrainment of chlorine-containing compounds via the organophosphorus catalyst system.

An important class of organophosphorus compounds is that of the organotetraphosphites or tetraphosphites for short, which are a ligand class of interest on the industrial scale.

WO 2014/177355 A1 describes a process for preparing organotetraphosphites having a Hostanox O3 lead structure (bis[3,3-bis-(4'-hydroxy-3'-tert-butylphenyl)butanoic acid] glycol ester or ethylenebis[3,3-bis(3-tert-butyl-4-hydroxyphenyl)butyrate]), and the use of these ligands in hydroformylation.

However, the aforementioned document does not describe a process for reducing the chlorine content of the organotetraphosphites.

It is therefore important to develop a production and purification process for organotetraphosphites which provides corresponding ligands having a low chloride content before they can be used in an industrial scale process.

This process should be applicable to a maximum number of organotetraphosphites, since the chlorine problem plays a fundamental role for any ligand before it can be used in an industrial scale plant.

The chloride content can be determined analytically in a simple manner, for example by aqueous titration. A more extensive determination is that of the total chlorine content, which, as well as the chlorides, also encompasses chlorine bound in other forms. Emphasis on the total chlorine content is also of material relevance, in that it cannot be ruled out that chlorine bound in other forms is also able to damage the reactor. In judging the limits for total chlorine, however, the chloride fraction remains crucial.

A suitable method for determining the total chlorine content is the combustion according to Wickbold with sample preparation to DIN 51408 and analysis by ion chromatography to DIN EN ISO 10304.

The patent literature discloses various methods for reducing the total chlorine content of organophosphorus ligands after the actual synthesis:

WO 2013/098368 A1 describes the purification of organodiphosphites, wherein the impurities to be removed include not just chloride ions but particularly diols, basic impurities, mono- and dioxides and secondary organophosphites. Owing to the different structure and associated different chemical characteristics of tetraphosphites and diphosphites, the purification process described in this prior document is not applicable to the purification of organotetraphosphites.

DE 10 2011 002 640 A1 discloses a process for purifying biphephos (6,6'-[(3,3'-di-tert-butyl-5,5'-dimethoxy-1,1'-biphenyl-2,2'-diyl)bis(oxy)]bis(dibenzo[d,f][1,3,2]dioxaphosphepine)). The process described therein is intended to reduce the chlorine content of biphephos. This is done by washing the biphephos with a solvent selected from ethyl acetate, anisole, ortho-xylene, toluene, acetone, 2-propanol and $C_5$-$C_{10}$-alkanes, or recrystallizing from such a solvent.

In this context, however, the long period needed to precipitate or crystallize the product is in need of improvement. The ligand is precipitated overnight, meaning that >8 hours are required. Moreover, it is pointed out in the examples that another solvent has to be added after the precipitation overnight, in order to complement the precipitation (Example 2 of DE 10 2011 002 640 A1). These long reaction times are problematic in industrial scale syntheses, since the effect of long residence times and hence ultimately long production times for the ligand is to increase the cost thereof.

Document EP 0 285 136 claims a process for purifying tertiary organophosphites to free them of secondary organophosphites. The process envisages treatment with a composition containing both tertiary and secondary organophosphites with water at elevated temperature in the presence of a Lewis base. Lewis bases used are inorganic salts (carbonates, hydroxides, oxides), tertiary amines and polymers which carry amine groups. The amount of water used and the amount of Lewis base used are each especially at least 0.5 to 1 equivalent based on the amount of secondary organophosphite.

Here, a significant disadvantage of the process claimed is that water is used not just in traces but in the aforementioned greater amounts. This is because not only the contaminants to be removed but also the tertiary organophosphites themselves react, such that a portion of the product of value is lost according to the hydrolysis stability of the organophosphites.

Document DE 10 2004 049 339 describes a process for purifying phosphorus chelate ligands by means of extraction using a polar extractant. The crude ligand was extracted here six times with a polar solvent, and then has a content of amine base, amine hydrochloride or mixtures thereof of less than 100 ppm. In this method of purification, however, enormous amounts of solvent are needed, which is in need of improvement from an economic and ecological point of view.

U.S. Pat. No. 3,980,739 discloses the purification of triaryl phosphites using $NH_3$ and/or $NH_2$—$NH_2$. The purification is effected here within a temperature range from 20° C. to 120° C. The bases used here are ammonia and hydrazine. Both compounds are classified as particularly toxic and carcinogenic under the globally harmonized system for classification and labelling of chemicals. Substitution for less hazardous compounds is thus desirable. Moreover, ammonia is used in the form of a gas, which requires special safety measures in the case of industrial scale use, and would make it preferable to use liquid reagents.

DE 10 2014 206 520 A1 discloses comparable structures, but does not give any pointer to the means of purification thereof.

The problem addressed by the present invention was thus that of developing a purifying process for organotetraphosphites in which the chlorine content is reduced, without this process having the above-described disadvantages.

A particular problem addressed was that of using the process to purify organotetraphosphites having a chlorine content of more than 1000 ppm to 100 000 ppm and especially of 2000 ppm to 100 000 ppm in the organotetraphosphite to a chlorine content of less than 1000 ppm in the organotetraphosphite. Preferably, the chlorine content was to be reduced to less than 500 ppm in the organotetraphosphite, and more preferably to less than 250 ppm in the organotetraphosphite. The chlorine contents reported are meant as total chlorine contents.

This is because the contaminated organotetraphosphite can contain organic chlorides and/or inorganic chlorides. Organic chlorides contain at least one carbon atom, whereas inorganic chlorides do not include any carbon. Contamination of the organophosphorus product by the following chlorides is particularly likely, since these chlorine-containing compounds are either required in the course of synthesis of organophosphorus compounds or are unavoidably produced as by-products:

phosphorus trichloride, chlorophosphites, dichlorophosphites, hydrochlorides of amines, hydrochlorides of alkali metals, chlorides of alkaline earth metals, chlorine-containing acids obtainable from the hydrolysis of phosphorus trichloride.

Therefore, the contaminated organotetraphosphite generally includes at least one of the chlorides enumerated.

This object is achieved by a process according to Claim 1.

Process for reducing the chlorine content in an organotetraphosphite of one of the general formulae I and II:

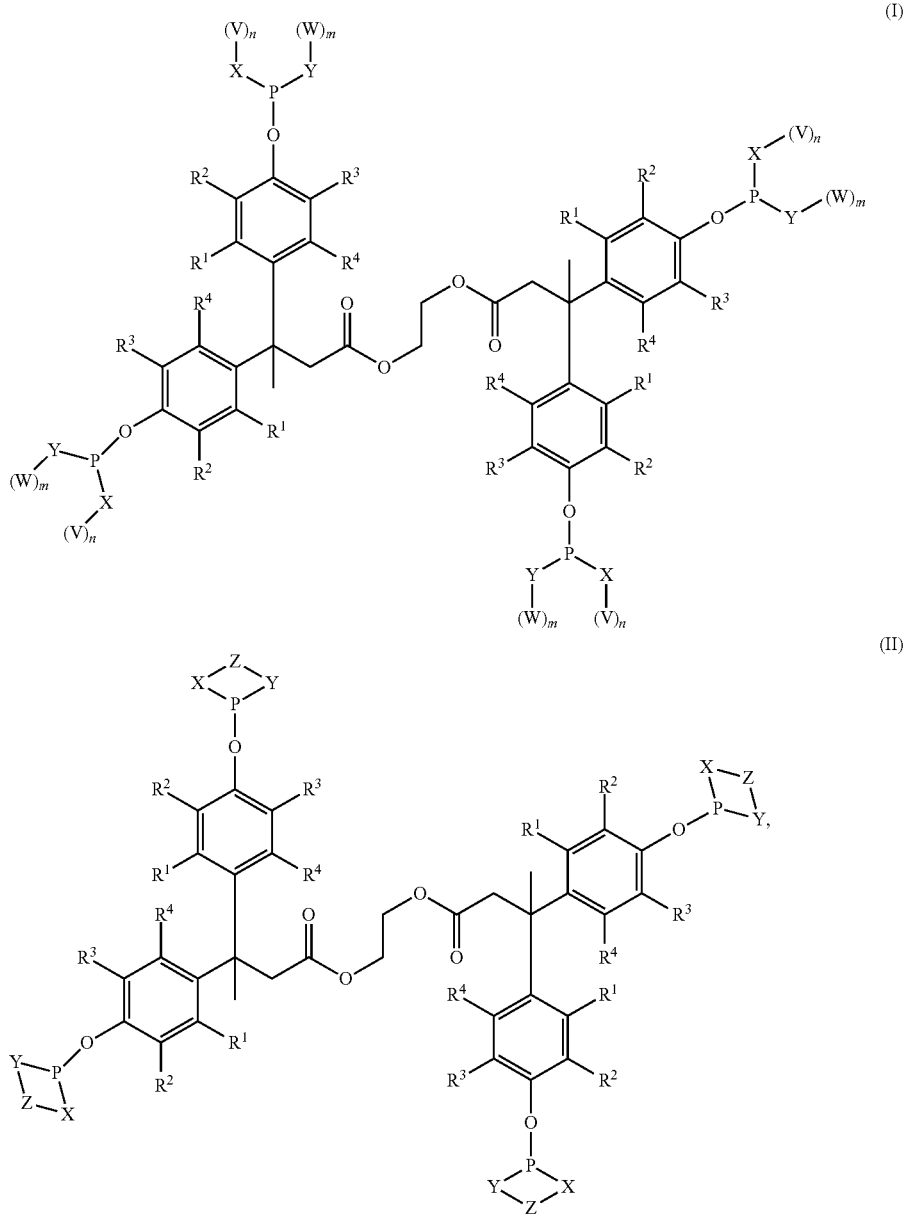

where
R¹, R², R³, R⁴ are each independently selected from: —H, —($C_1$-$C_{12}$)-alkyl;
V and W are each independently selected from:
—H, —($C_1$-$C_{12}$)-alkyl, —O—($C_1$-$C_{12}$)-alkyl, —($C_1$-$C_{12}$)-heteroalkyl, —($C_4$-$C_{20}$)-aryl, —($C_4$-$C_{20}$)-aryl-($C_1$-$C_{12}$)-alkyl, —($C_4$-$C_{20}$)-aryl-O—($C_1$-$C_{12}$)-alkyl, —($C_1$-$C_{12}$)-alkyl-($C_4$-$C_{20}$)-aryl, —($C_4$-$C_{20}$)-aryl-COO—($C_1$-$C_{12}$)-alkyl, —($C_4$-$C_{20}$)-aryl-CONH—($C_1$-$C_{12}$)-alkyl, —($C_4$-$C_{20}$)-aryl-CON[($C_1$-$C_{12}$)-alkyl]$_2$, —($C_4$-$C_{20}$)-heteroaryl, —($C_4$-$C_{20}$)-heteroaryl-($C_1$-$C_{12}$)-alkyl, —($C_3$-$C_{12}$)-cycloalkyl, —($C_3$-$C_{12}$)-cycloalkyl-($C_1$-$C_{12}$)-alkyl, —($C_3$-$C_{12}$)-heterocycloalkyl, —($C_3$-$C_{12}$)-heterocycloalkyl-($C_1$-$C_{12}$)-alkyl, —CO—($C_1$-$C_{12}$)-alkyl, —CO—($C_4$-$C_{20}$)-aryl, —CO—($C_4$-$C_{20}$)-heteroalkyl, —($C_4$-$C_{20}$)-aryl-CO—($C_1$-$C_{12}$)-alkyl, —($C_4$-$C_{20}$)-aryl-CO—($C_4$-$C_{20}$)-aryl;

X and Y are each independently selected from O and N;
where, in the case that X is O, n=1,
and, in the case that Y is O, m=1,
and, in the case that X is N, n=1 or 2,
and, in the case that Y is N, m=1 or 2;
Z is selected from:
—($C_1$-$C_{14}$)-alkyl-, —($C_4$-$C_{20}$)-aryl-, —($C_4$-$C_{20}$)aryl-($C_1$-$C_{12}$)-alkyl-, —($C_1$-$C_{14}$)-heteroalkyl-, —($C_4$-$C_{20}$)-heteroaryl-, —CO—($C_4$-$C_{14}$)-heteroaryl-, —CO—($C_4$-$C_{20}$)-aryl-, —($C_3$-$C_{12}$)-cycloalkyl-, —($C_3$-$C_{12}$)-heterocycloalkyl-, —($C_4$-$C_{20}$)-aryl-CO—($C_4$-$C_{20}$)-aryl-, —($C_1$-$C_{14}$)-alkyl-O—($C_1$-$C_{14}$)-alkyl-;
where the alkyl, heteroalkyl, cycloalkyl, heterocycloalkyl, aryl and heteroaryl groups mentioned are optionally mono- or polysubstituted;
comprising the following process steps:
a) contacting the organotetraphosphite with a solution comprising at least one solvent and at least one base, where the at least one solvent is selected from aromatics, alcohols, acetone, ethyl acetate, acetonitrile and ethers, and where the at least one base is selected from amine bases, alkoxides, pyridine, pyridine derivatives, N-methyl-2-pyrrolidone, triethylamine and triethanolamine, b) adjusting the temperature to a value in the range from −20° C. to +15° C., c) removing the purified organotetraphosphite.

In the cases in which X and/or Y is/are N too, compounds having a structure according to I or II are also referred to as organotetraphosphites for the purposes of the invention, even when they would more correctly be referred to as organotetraphosphoramidites because of the P—N bond.

Optionally, the solution with which the organotetraphosphite is contacted in step a) of the process contains, as well as the at least one solvent and the at least one base, also traces of water (max. 5% based on the solvent content) and/or the at least one solvent and/or the at least one base contains water. In the case of a solution containing traces of water, the water content based on the solvent content is preferably up to 5%, especially 1% to 2% or <1%.

The aforementioned optional traces of water can alternatively also not be added until during or after the contacting of the organotetraphosphite with the solution containing the base and the solvent in step a). In this case, the solution with which the organotetraphosphite is contacted in step a) does not contain any water at first, meaning that the at least one base present in the solution and the at least one solvent are anhydrous. In this embodiment, however, a small amount of water, namely up to 5%, especially 1% to 2% or <1% based on the solvent content, is added subsequently to the solution containing the organotetraphosphite.

Solvents are considered here to be anhydrous when they include only traces of water (<50 ppm).

The at least one base present in the solution suppresses unwanted side reactions that would take place, for example, in the presence of water or alcohols, for example an alcoholysis or transesterification. The at least one base preferably additionally has the advantage that the chlorine originally present in the organotetraphosphite dissolves therein.

In the context of the invention, alkyl represents an unbranched or branched aliphatic radical. $(C_1-C_{12})$-Alkyl and $O-(C_1-C_{12})$-alkyl may each be unsubstituted or substituted by one or more identical or different radicals selected from $(C_3-C_{12})$-cycloalkyl, $(C_3-C_{12})$-heterocycloalkyl, $(C_6-C_{20})$-aryl, fluorine, chlorine, cyano, formyl, acyl and alkoxycarbonyl.

$(C_3-C_{12})$-Cycloalkyl and $(C_3-C_{12})$-heterocycloalkyl may each be unsubstituted or substituted by one or more identical or different radicals selected from $(C_1-C_{12})$-alkyl, $(C_1-C_2)$-alkoxy, $(C_3-C_{12})$-cycloalkyl, $(C_3-C_{12})$-heterocycloalkyl, $(C_6-C_{20})$-aryl, fluorine, chlorine, cyano, formyl, acyl and alkoxycarbonyl.

$(C_4-C_{20})$-Aryl may each be unsubstituted or substituted by one or more identical or different radicals selected from $(C_1-C_{12})$-alkyl, $(C_1-C_{12})$-alkoxy, $(C_3-C_{12})$-cycloalkyl, $(C_3-C_{12})$-heterocycloalkyl, $(C_6-C_{20})$-aryl, fluorine, chlorine, cyano, formyl, acyl and alkoxycarbonyl.

In the context of the invention, the expression "—$(C_1-C_{12})$-alkyl" encompasses straight-chain and branched alkyl groups. Preferably, these groups are unsubstituted straight-chain or branched —$(C_1-C_8)$-alkyl groups and most preferably —$(C_1-C_6)$-alkyl groups. Examples of —$(C_1-C_{12})$-alkyl groups are especially methyl, ethyl, propyl, isopropyl, n-butyl, isobutyl, sec-butyl, tert-butyl, n-pentyl, 2-pentyl, 2-methylbutyl-, 3-methylbutyl-, 1,2-dimethylpropyl-, 1,1-dimethylpropyl, 2,2-dimethylpropyl-, 1-ethylpropyl-, n-hexyl-, 2-hexyl-, 2-methylpentyl-, 3-methylpentyl-, 4-methylpentyl-, 1,1-dimethylbutyl-, 1,2-dimethylbutyl-, 2,2-dimethylbutyl-, 1,3-dimethylbutyl-, 2,3-dimethylbutyl-, 3,3-dimethylbutyl-, 1,1,2-trimethylpropyl-, 1,2,2-trimethylpropyl-, 1-ethylbutyl-, 1-ethyl-2-methylpropyl-, n-heptyl-, 2-heptyl-, 3-heptyl-, 2-ethylpentyl-, 1-propylbutyl-, n-octyl-, 2-ethylhexyl-, 2-propylheptyl-, nonyl-, decyl.

The elucidations relating to the expression "—$(C_1-C_{12})$-alkyl" also apply to the alkyl groups in —O—$(C_1-C_{12})$-alkyl, i.e. in —$(C_1-C_{12})$-alkoxy. Preferably, these groups are unsubstituted straight-chain or branched —$(C_1-C_6)$-alkoxy groups.

Substituted —$(C_1-C_{12})$-alkyl groups and substituted —$(C_1-C_{12})$-alkoxy groups may have one or more substituents, depending on their chain length. The substituents are preferably independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl and alkoxycarbonyl.

The expression "—$(C_3-C_{12})$-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl or adamantyl.

The expression "—$(C_3-C_{12})$-heterocycloalkyl groups", in the context of the present invention, encompasses nonaromatic, saturated or partly unsaturated cycloaliphatic groups having 3 to 12, especially 5 to 12, carbon atoms. The —$(C_3-C_{12})$-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(═O)—, —C(═O)— and —S(═O)—. Examples of —$(C_3-C_{12})$-heterocycloalkyl groups are tetrahydrothiophenyl, tetrahydrofuryl, tetrahydropyranyl and dioxanyl.

Substituted —$(C_3-C_{12})$-cycloalkyl groups and substituted —$(C_3-C_{12})$-heterocycloalkyl groups may have one or more (e.g. 1, 2, 3, 4 or 5) further substituents, depending on their ring size. These substituents are preferably each independently selected from —$(C_1-C_{12})$-alkyl, —$(C_1-C_{12})$-alkoxy, —$(C_3-C_{12})$-cycloalkyl, —$(C_3-C_{12})$-heterocycloalkyl, —$(C_6-C_{20})$-aryl, fluorine, chlorine, cyano, formyl, acyl and alkoxycarbonyl. Substituted —$(C_3-C_{12})$-cycloalkyl groups preferably bear one or more —$(C_1-C_6)$-alkyl groups. Substituted —$(C_3-C_{12})$-heterocycloalkyl groups preferably bear one or more —$(C_1-C_6)$-alkyl groups.

In the context of the present invention, the expression "—$(C_4-C_{20})$-aryl" encompasses mono- or polycyclic aromatic hydrocarbyl radicals. These have 4 to 20 ring atoms, more preferably 6 to 14 ring atoms, especially 6 to 10 ring atoms. Aryl is preferably —$(C_6-C_{10})$-aryl. Aryl is especially phenyl, naphthyl, indenyl, fluorenyl, anthracenyl, phenanthrenyl, naphthacenyl, chrysenyl, pyrenyl, coronenyl, biphenyl. More particularly, aryl is phenyl, biphenyl, naphthyl and anthracenyl.

Substituted —$(C_4-C_{20})$-aryl groups may have one or more (e.g. 1, 2, 3, 4 or 5) substituents, depending on the ring size. These substituents are preferably each independently selected from —$(C_1-C_{12})$alkyl, —$(C_1-C_{12})$-alkoxy, —$(C_3-C_{12})$-cycloalkyl, —$(C_3-C_{12})$-heterocycloalkyl, —$(C_6-C_{20})$-aryl, fluorine, chlorine, cyano, formyl, acyl and alkoxycarbonyl.

Substituted —$(C_4-C_{20})$-aryl groups are preferably substituted —$(C_6-C_{10})$-aryl groups, especially substituted phenyl, substituted biphenyl, substituted naphthyl or substituted anthracenyl. Substituted —(C$_4$-C$_{20}$)-aryl groups preferably bear one or more, for example 1, 2, 3, 4 or 5, substituents, selected from —(C$_1$-C$_{12}$)-alkyl groups, —(C$_1$-C$_{12}$)-alkoxy groups.

In one embodiment of the process according to the invention, V and W are each independently selected from:
—H, —(C$_1$-C$_{12}$)-alkyl, —O—(C$_1$-C$_{12}$)-alkyl, —(C$_1$-C$_{12}$)-heteroalkyl, —(C$_4$-C$_{20}$)-aryl, —(C$_4$-C$_{20}$)-aryl-(C$_1$-C$_{12}$)-alkyl, —(C$_4$-C$_{20}$)-aryl-O—(C$_1$-C$_{12}$)-alkyl, —(C$_1$-C$_{12}$)-alkyl-(C$_4$-C$_{20}$)-aryl, —(C$_4$-C$_{20}$)-aryl-COO—(C$_1$-C$_{12}$)-alkyl, —(C$_4$-C$_{20}$)-heteroaryl, —(C$_3$-C$_{12}$)-cycloalkyl, —(C$_3$-C$_{12}$)-heterocycloalkyl, —(C$_3$-C$_{12}$)-heterocycloalkyl-(C$_1$-C$_{12}$)-alkyl, —CO—(C$_1$-C$_{12}$)-alkyl, —CO—(C$_4$-C$_{20}$)-aryl, —CO—(C$_4$-C$_{20}$)-heteroalkyl, —(C$_4$-C$_{20}$)-aryl-CO—(C$_1$-C$_{12}$)-alkyl, —(C$_4$-C$_{20}$)-aryl-CO—(C$_4$-C$_{20}$)-aryl.

In one embodiment, V and W are each independently selected from:
—H, —(C$_1$-C$_{12}$)-alkyl, —O—(C$_1$-C$_{12}$)-alkyl, —(C$_4$-C$_{20}$)-aryl, —(C$_4$-C$_{20}$)-aryl-(C$_1$-C$_{12}$)-alkyl, —(C$_4$-C$_{20}$)-aryl-O—(C$_1$-C$_{12}$)-alkyl, —(C$_1$-C$_{12}$)-alkyl-(C$_4$-C$_{20}$)-aryl, —(C$_4$-C$_{20}$)-aryl-COO—(C$_1$-C$_{12}$)-alkyl.

In one embodiment, V and W are, or just one of the substituents V and W is,

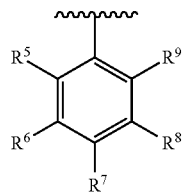

where $R^5$, $R^6$, $R^7$, $R^8$, $R^9$ are each independently selected from —H, —(C$_1$-C$_{12}$)-alkyl, —O—(C$_1$-C$_{12}$)-alkyl, -phenyl, —COO—(C$_1$-C$_{12}$)-alkyl.

In one embodiment, V and W are the same radical.
In one embodiment, Z is selected from:
—(C$_1$-C$_{14}$)-alkyl-, —(C$_4$-C$_{20}$)-aryl-, —(C$_4$-C$_{20}$)-aryl-(C$_1$-C$_{12}$)-alkyl-, —(C$_4$-C$_{20}$)-heteroaryl-, —CO—(C$_4$-C$_{14}$)-heteroaryl-, —CO—(C$_4$-C$_{20}$)-aryl-.

In one variant of the process, Z is selected from:

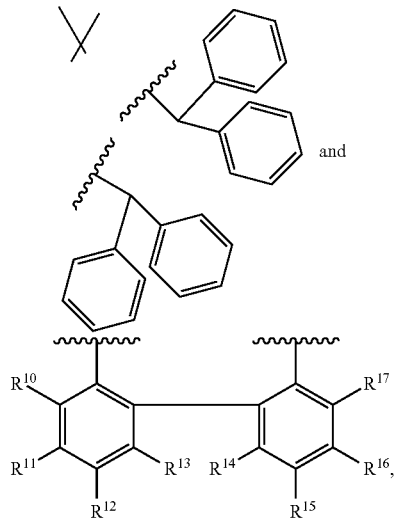

where $R^{10}$, $R^{11}$, $R^{12}$, $R^{13}$, $R^{14}$, $R^{15}$, $R^{16}$, $R^{17}$ are each independently selected from:
—H, —(C$_1$-C$_{12}$)-alkyl, —O—(C$_1$-C$_{12}$)-alkyl, —O—(C$_6$-C$_{20}$)-aryl, —(C$_6$-C$_{20}$)-aryl, -halogen (such as Cl, F, Br, I), —COO—(C$_1$-C$_{12}$)-alkyl, —CONH—(C$_1$-C$_{12}$)-alkyl, —(C$_6$-C$_{20}$)-aryl-CON[(C$_1$-C$_{12}$)-alkyl]$_2$, —CO—(C$_1$-C$_{12}$)-alkyl, —CO—(C$_6$-C$_{20}$)-aryl, —COOH, —OH, —SO$_3$H, —SO$_3$Na, —NO$_2$, —CN, —NH$_2$, —N[(C$_1$-C$_{12}$)-alkyl]$_2$.

In one variant of the process, $R^{10}$, $R^{11}$, $R^{12}$, $R^{13}$, $R^{14}$, $R^{15}$, $R^{16}$, $R^{17}$ are each independently selected from:
—H, —(C$_1$-C$_{12}$)-alkyl, —O—(C$_1$-C$_{12}$)-alkyl.

In one embodiment, $R^1$, $R^3$, $R^4$ are —H.
In one embodiment, $R^2$ is —(C$_1$-C$_{12}$)-alkyl.
Preference is given here to tert-butyl,
In one embodiment, X and Y are O.
In one embodiment, X and Y are N.
In one embodiment, X and Y are O, where the latter is bonded to a phenyl radical which may in turn be substituted, and may also be part of a larger fused aromatic system.

In one variant of the process, the at least one solvent is selected from: ethyl acetate, anisole, ortho-xylene, toluene, acetone, methanol, ethanol, propanol, isopropanol, acetonitrile.

Preferably, the at least one solvent is selected from: acetonitrile, ethyl acetate, ethanol, propanol, toluene.

More preferably, the at least one solvent is ethanol.

In one variant of the process, the at least one base is selected from: triethylamine, dimethylaminobutane (DMAB), pentylamine, hexylamine, dibutylamine, N-methyl-2-pyrrolidone (NMP), triethanolamine, sodium methoxide, sodium ethoxide, pyridine, dimethylaminopyridine (DMAP).

In one variant of the process, the at least one base is an amine base.

Preferably, the at least one base is selected from: triethylamine, dimethylaminobutane (DMAB), sodium methoxide, sodium ethoxide, pyridine, dimethylaminopyridine (DMAP).

More preferably, the at least one base is selected from dimethylaminobutane (DMAB) and triethylamine.

In one variant of the process, the contacting in step a) is effected by adding the solvent and the base to the solid organotetraphosphite, for example at room temperature, and stirring the suspension formed for at least one hour. In the course of this, the chlorinated impurities preferably go into solution, while the organotetraphosphite remains predominantly undissolved.

In one variant of the process, after step a) but before step c), a further solvent selected from aromatics, alcohols, acetone, ethyl acetate, acetonitrile and ethers is added to the solution.

In a further variant of the process, the temperature in process step b) to a value to set in the range from −20° C. to +10° C., especially in the range from −10° C. to +10° C., as a result of which any organotetraphosphite that has gone into solution is precipitated out again.

In one variant of the process, the purified organotetraphosphite is separated from the solution in step c) by filtration.

In one variant of the process, the organotetraphosphite which is contacted in step a) with the solution containing the at least one solvent and the at least one base has a chlorine content of 1500 ppm to 100 000 ppm.

In a further variant of the process, the organotetraphosphite which is contacted in step a) with the solution containing the at least one solvent and the at least one base has a chlorine content of 5000 ppm to 100 000 ppm.

The chlorine contents reported are meant as total chlorine contents.

The total chlorine content is determined according to Wickbold: sample preparation to DIN 51408 and analysis by ion chromatography to DIN EN ISO 10304.

In one variant of the process for reducing the chlorine content, an organotetraphosphite of one of the general formulae I and II:

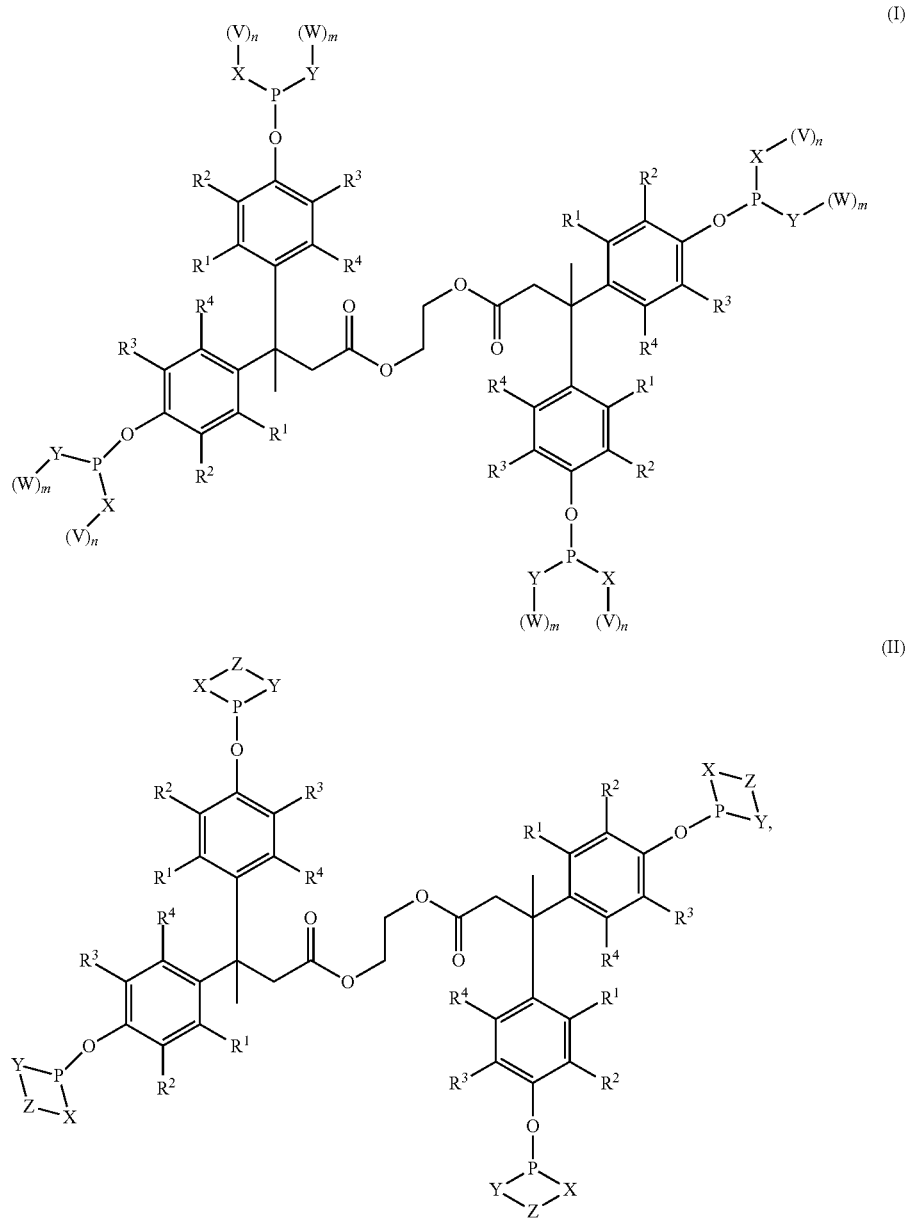

is purified,
where
$R^2$ is tert-butyl and where $R^1$, $R^3$ and $R^4$ are —H.

More preferably, the process according to the invention serves for preparation of organotetraphosphites of one of the structural formulae III, IV, V, VI, VII, VIII, IX, X, XI, XII, XIII, XIV and XV:

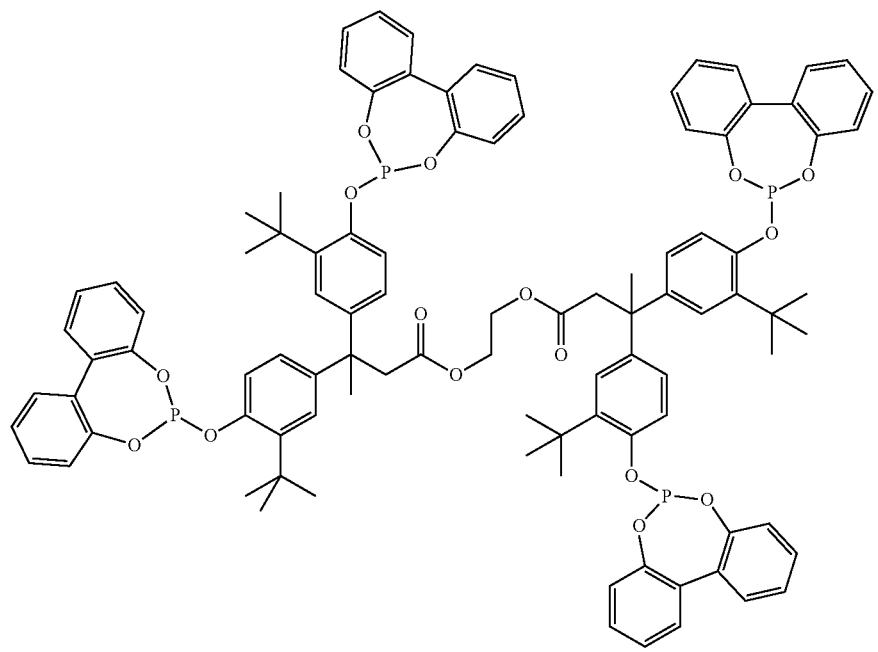
(III)
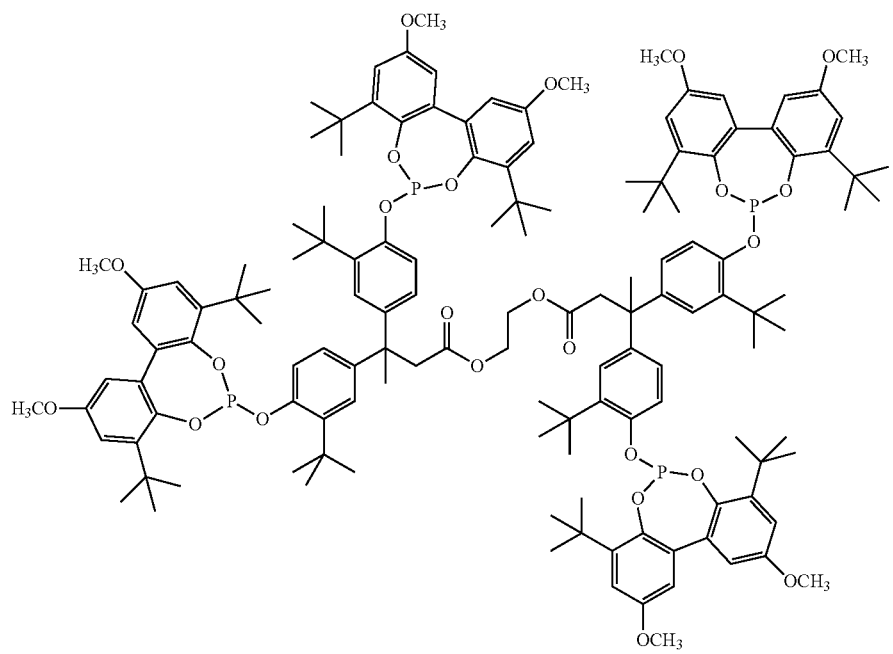
(IV)

(V)
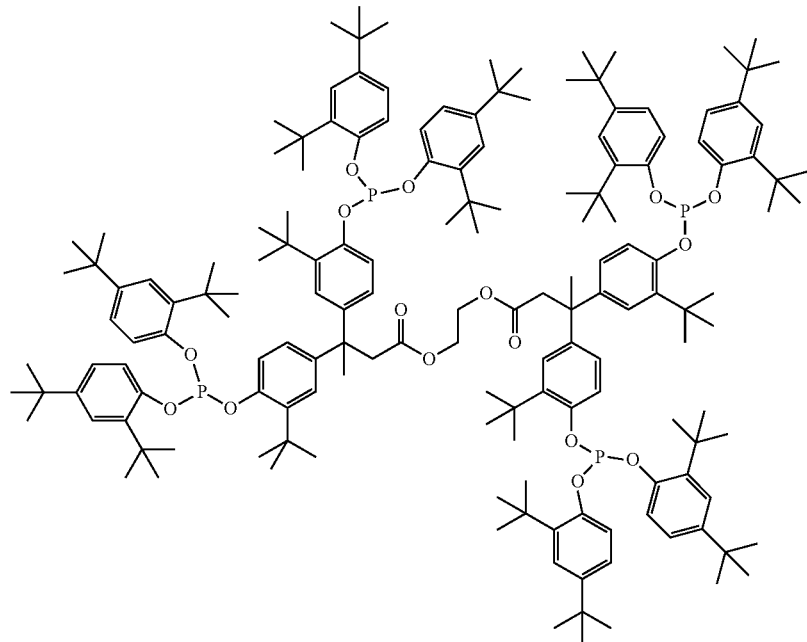
(VI)
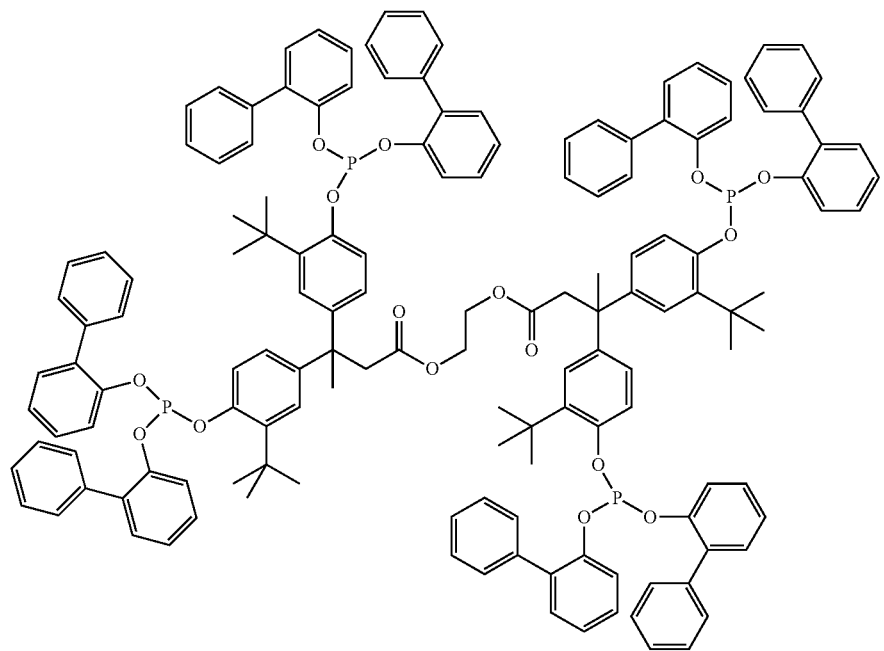

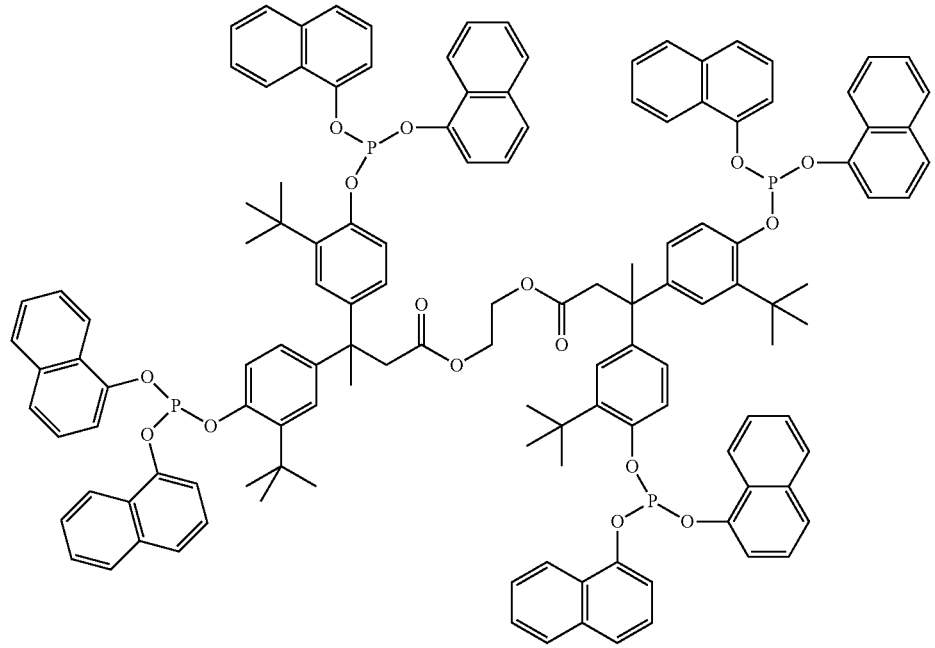
(VII)
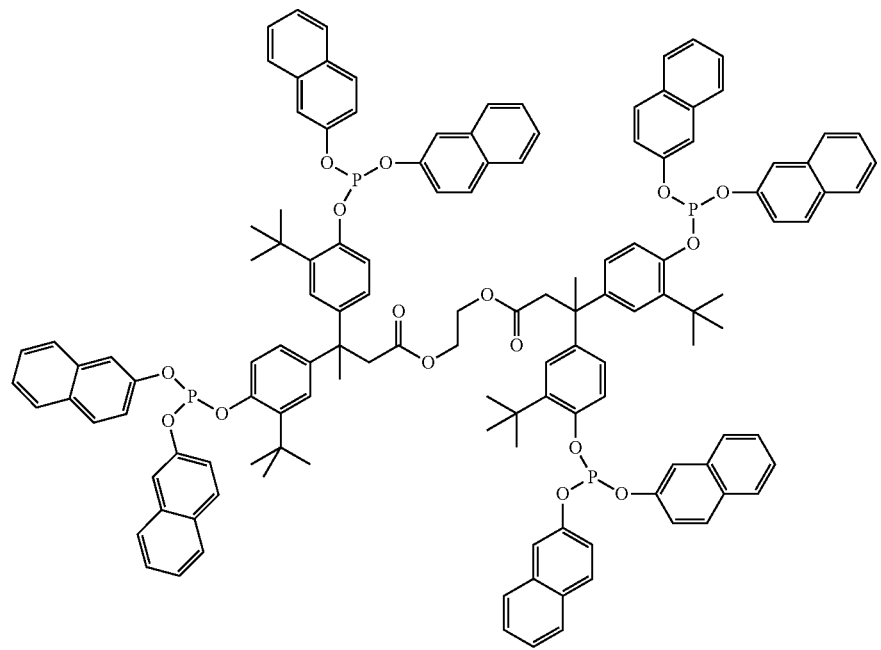
(VIII)

-continued
(IX)
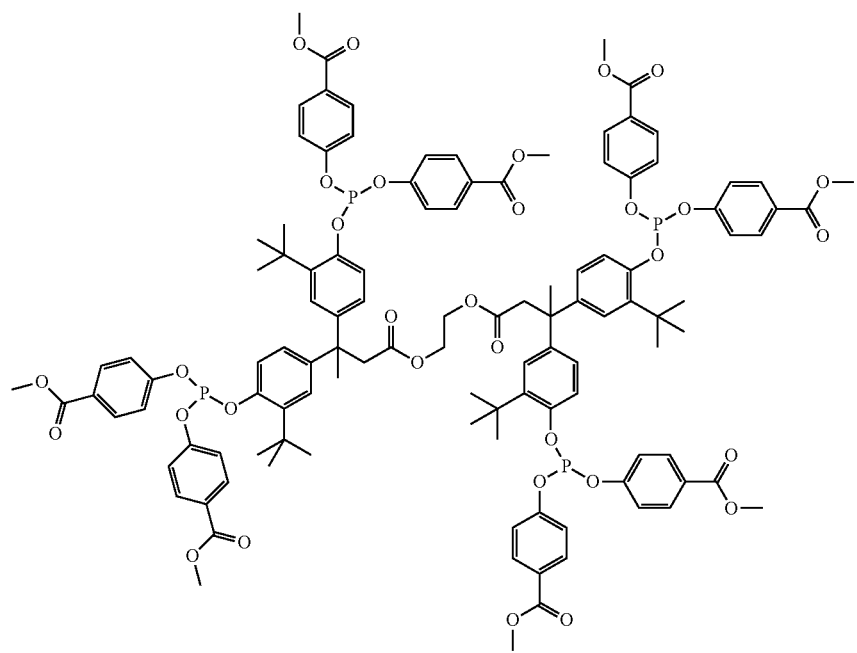
(X)
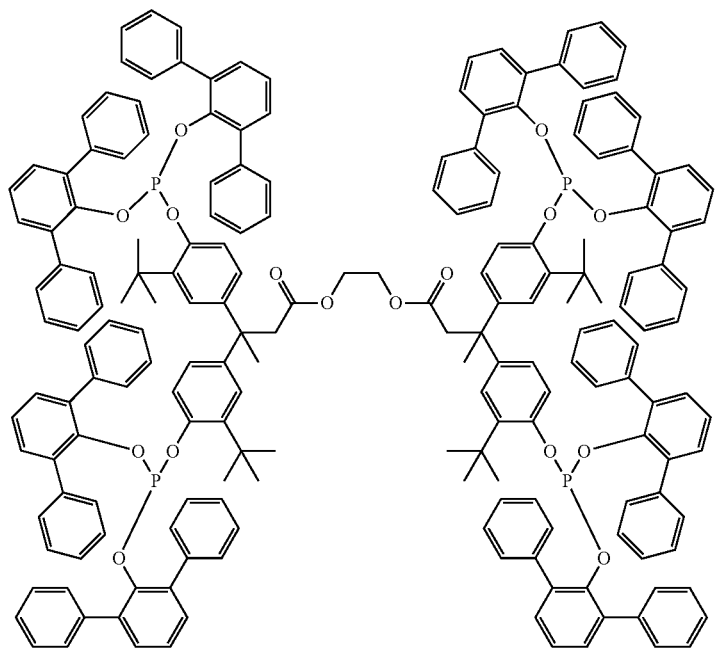

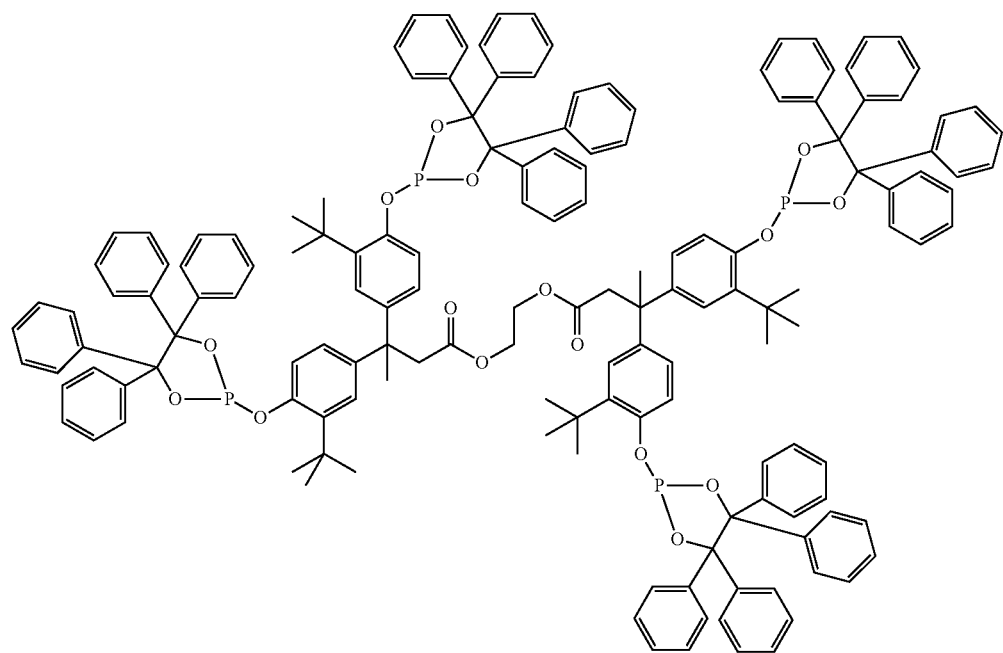
(XI)
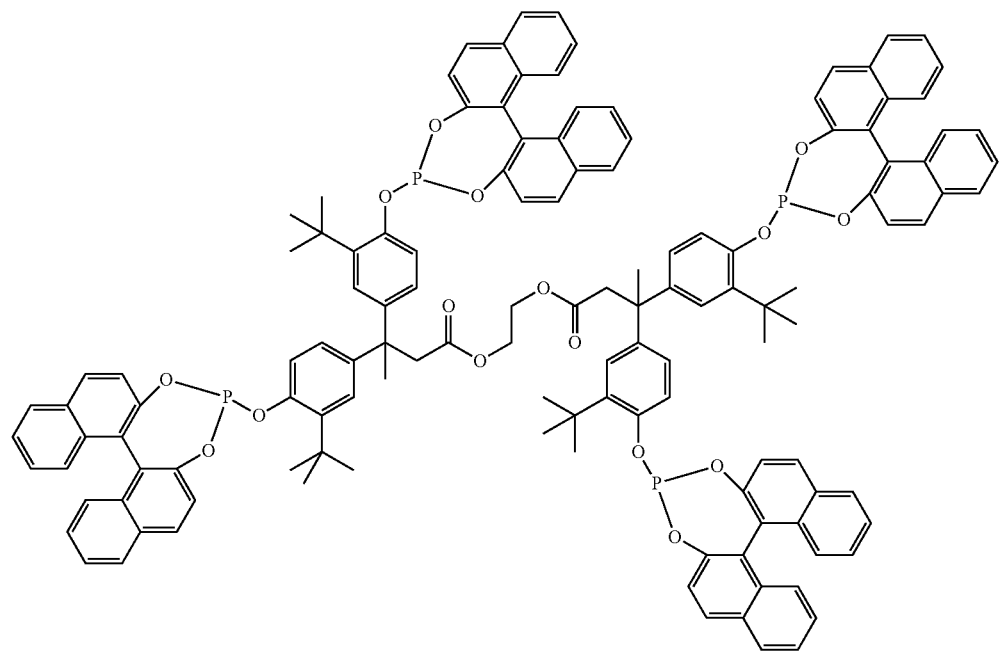
(XII)

(XIII)
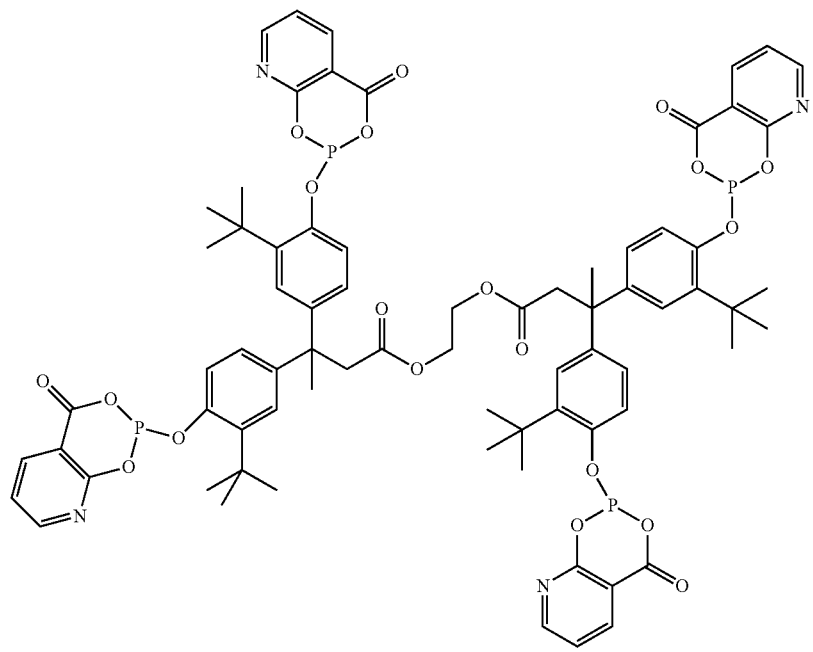
(XIV)
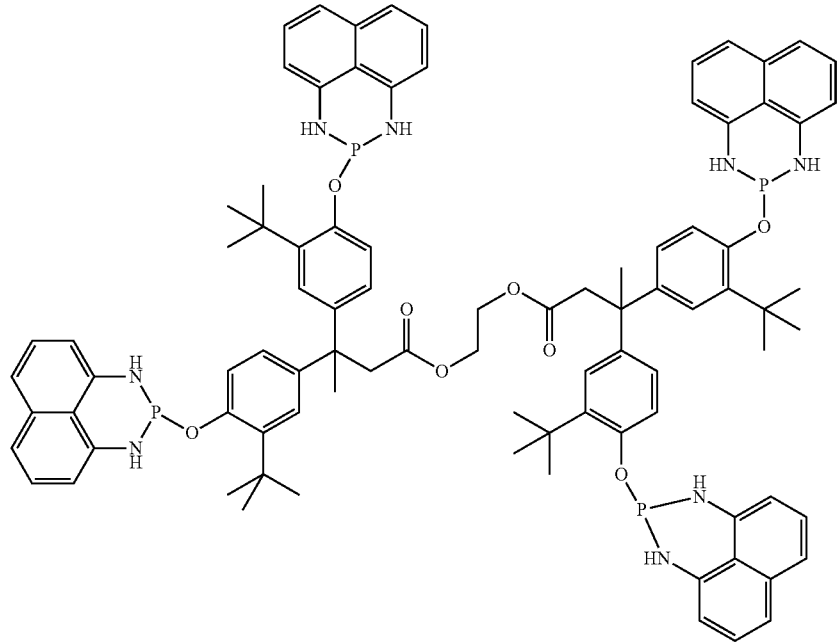

(XV)

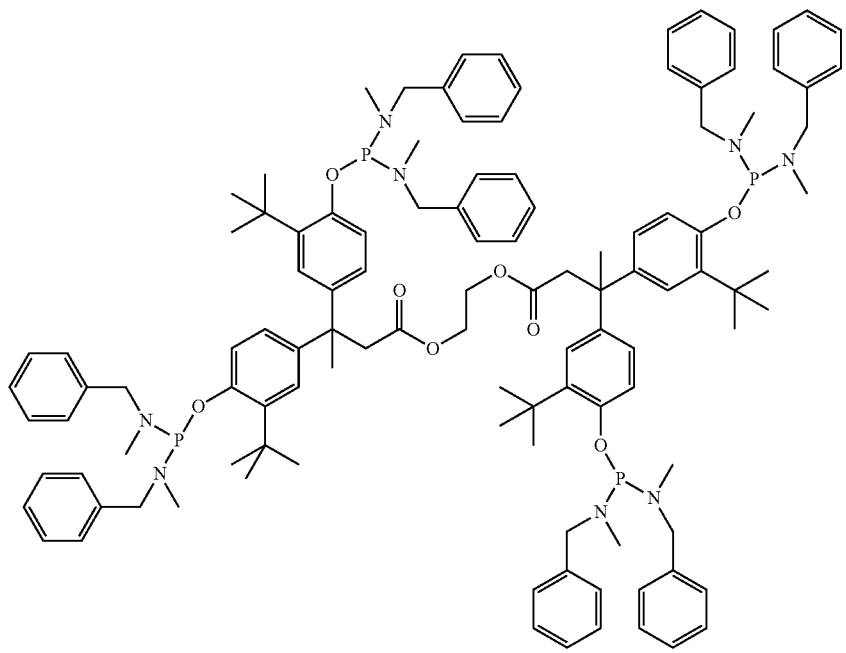

The process claimed may also have upstream process steps, for example the synthesis of the organotetraphosphites. In that case, these process steps precede process step a).

In a synthesis of the ligand upstream of process step a), the organotetraphosphite can be isolated on completion of crystallization. This is typically accomplished by filtering off and, optionally, drying the filtered-off organotetraphosphite.

The invention is to be illustrated in detail hereinafter by working examples.

General Procedures

The total chlorine content reported in connection with this invention is determined according to Wickbold: sample preparation to DIN 51408 and analysis by ion chromatography to DIN EN ISO 10304.

All the preparations which follow were carried out under protective gas using standard Schlenk techniques. Unless stated otherwise, the solvents were dried over suitable desiccants before use (Purification of Laboratory Chemicals, W. L. F. Armarego (Author), Christina Chai (Author), Butterworth Heinemann (Elsevier), 6th edition, Oxford 2009).

Phosphorus trichloride (Aldrich) was distilled under argon before use. All preparative operations were effected in baked-out vessels. The products were characterized by means of NMR spectroscopy. Chemical shifts are reported in ppm.

The $^{31}P$ NMR signals were referenced as follows: $SR_{31P} = SR_{1H}*(BF_{31P}/BF_{1H}) = SR_{1H}*0.4048$ (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

The recording of nuclear resonance spectra was effected on Bruker Avance 300 or Bruker Avance 400, gas chromatography analysis on Agilent GC 7890A, elemental analysis on Leco TruSpec CHNS and Varian ICP-OES 715, and ESI-TOF mass spectrometry on Thermo Electron Finnigan MAT 95-XP and Agilent 6890 N/5973 instruments.

Hostanox O3 (bis[3,3-bis(4'-hydroxy-3'-tert-butylphenyl) butanoic acid] glycol ester or ethylenebis[3,3-bis(3-tert-butyl-4-hydroxyphenyl)butyrate]) is commercially available and was purchased from Clariant.

To supplement the synthesis methods which follow, the preparation of organotetraphosphites having a Hostanox O3 lead structure (bis[3,3-bis(4'-hydroxy-3'-tert-butylphenyl) butanoic acid] glycol ester or ethylenebis[3,3-bis(3-tert-butyl-4-hydroxyphenyl)butyrate]) is also described in detail in WO 2014/177355 A1.

In each of the syntheses of the organotetraphosphites V, VI, VII, VIII, IX, X, XIII, XIV and XV described in Examples 3a, 4 to 8 and 11 to 13, the reactant used is the chlorophosphite (10):

(10)

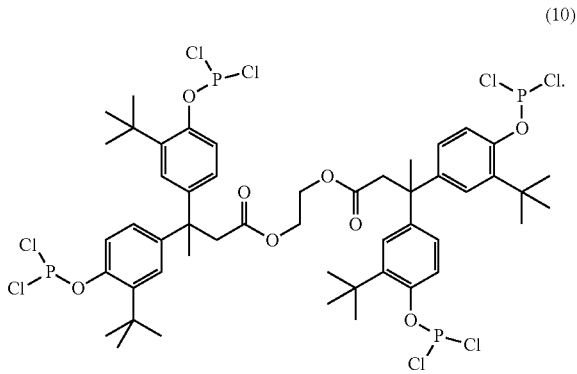 [SMILES: CC(C)(C)c1cc(C(C)(CC(=O)OCCOC(=O)CC(C)(c2ccc(OP(Cl)Cl)c(C(C)(C)C)c2)c2ccc(OP(Cl)Cl)c(C(C)(C)C)c2)c2ccc(OP(Cl)Cl)c(C(C)(C)C)c2)ccc1OP(Cl)Cl]

The chlorophosphite (10) was obtained as follows:

To a solution of phosphorus trichloride (0.66 g; 4.81 mmol) in THF (3 ml) is added dropwise while stirring at 0° C. a mixture of Hostanox O3 (ethylenebis[3,3-bis(3-tert-butyl-4-hydroxyphenyl)butyrate]) (0.796 g; 1.001 mmol), triethylamine (1.12 ml) and THF (30 ml). The mixture is left to stir at room temperature overnight, the filtrate is concentrated under reduced pressure and the residue obtained is dried at 50° C./0.1 mbar for 2 h. The product is dissolved in toluene (15 ml), and the solution is filtered through a G4 frit and concentrated to dryness.

Yield: 0.935 g (0.78 mmol; 78%). The product thus obtained was used further directly. $^{31}$P-NMR (CD$_2$Cl$_2$): 185.8 (s) ppm. $^1$H-NMR (CD$_2$Cl$_2$): 1.35 (36 H); 1.89 (6 H); 3.13 (4 H); 3.89 (4 H), 7.08 . . . 7.43 (12 H) ppm.

EXAMPLE 1

Synthesis of (III)

To a stirred solution of 6-chlorodibenzo[d,f][1,3,2]dioxaphosphepine (0.548 g; 2.188 mmol) in THF (4 ml) is added dropwise at 0° C. a mixture of Hostanox 03 (ethylenebis[3,3-bis(3-tert-butyl-4-hydroxyphenyl)butyrate]) (0.395 g; 0.497 mmol), triethylamine (0.62 ml) and THF (6 ml). The mixture is left to stir at room temperature overnight and filtered, the filtrate is concentrated under reduced pressure and the residue obtained is dried at 50° C./0.1 mbar for 2 h.

Purification by column chromatography (hexane/dichloromethane, 1:4, R$_f$=0.4) gives 0.449 g (0.272 mmol; 54%) of the tetraphosphite (III).

Analysis (calc. for C$_{96}$H$_{94}$O$_{16}$P$_4$=1651.68 g/mol): C, 71.41 (71.26) %; H, 5.73 (5.74) %; P, 7.53 (7.50) %.

$^{31}$P-NMR (CD$_2$Cl$_2$): 145.4 (s) ppm. $^1$H-NMR (CD$_2$Cl$_2$): 1.37 (36 H); 1.92 (6 H); 3.17 (4 H); 3.93 (4 H); 7.07 . . . 7.59 (44 H) ppm.

ESI-TOF HRMS: m/e 1652.55888 (M+H)$^+$.

EXAMPLE 2

Synthesis of (IV)

To a stirred solution of 4,8-di-tert-butyl-6-chloro-2,10-dimethoxydibenzo[d,f][1,3,2]dioxaphosphepine (2.387 g; 5.644 mmol) in THF (12 ml) is added dropwise at 0° C. a mixture of Hostanox 03 (ethylenebis[3,3-bis(3-tert-butyl-4-hydroxyphenyl)butyrate]) (1.019 g; 1.282 mmol), triethylamine (1.6 ml) and THF (12 ml). The mixture is left to stir at room temperature overnight and filtered, the filtrate is concentrated under reduced pressure and the residue obtained is dried at 50° C./0.1 mbar for 2 h. Purification by column chromatography (hexane/dichloromethane, 1:8, R$_f$=0.28) gives 1.437 g (0.614 mmol; 48%) of the tetraphosphite (IV).

Analysis (calc. for C$_{138}$H$_{174}$O$_{24}$P$_4$=2340.74 g/mol): C, 70.82 (70.81) %; H, 7.57 (7.49) %; P, 5.19 (5.29) %.

$^{31}$P-NMR (CD$_2$Cl$_2$): 139.9 (s) ppm. $^1$H-NMR (CD$_2$Cl$_2$): 1.27 (36 H); 1.43 (72 H); 1.93 (6 H); 3.16 (4 H); 3.88 (24 H), 3.93 (4 H), 6.83 . . . 7.17 (28 H) ppm.

ESI-TOF HRMS: m/e 2341.14642 (M+H)$^+$.

EXAMPLE 3

Synthesis of (V)

To a stirred solution of bis(2,4-di-tert-butylphenyl)phosphorochloridite (3.381 g; 7.086 mmol) in THF (15 ml) is added dropwise at 0° C. a mixture of Hostanox 03 (ethylenebis[3,3-bis(3-tert-butyl-4-hydroxyphenyl)butyrate]) (1.280 g; 1.61 mmol), triethylamine (2 ml) and THF (15 ml). The mixture is left to stir at room temperature overnight and filtered, the filtrate is concentrated under reduced pressure and the residue obtained is dried at 50° C./0.1 mbar for 2 h.

Purification by column chromatography (hexane/dichloromethane, 1:1, R$_f$=0.57) gives 3.6 g (1.41 mmol; 87%) of the tetraphosphite (V).

Analysis (calc. for C$_{162}$H$_{230}$O$_{16}$P$_4$=2557.44 g/mol): C, 76.26 (76.08) %; H, 9.05 (9.06) %; P, 4.93 (4.84) %.

$^{31}$P-NMR (CD$_2$Cl$_2$): 130.7 (s) ppm. $^1$H-NMR (CD$_2$Cl$_2$): 1.37 (72 H); 1.39 (36 H); 1.47 (72 H); 1.91 (6 H); 3.16 (4 H); 3.92 (4 H), 7.00. 7.47 (36 H) ppm.

ESI-TOF HRMS: m/e 518.37751; 647.46192; 1135.27566.

EXAMPLE 3a

Alternative Synthesis of (V)

In a 250 ml Schlenk flask, 9.2 g (0.044 mol) of 2,4-di-tert-butylphenol were admixed with 140 ml of dried toluene and 7 ml (0.050 mol) of triethylamine.

In a 500 ml Schlenk flask, 7.2 g (0.005 mol) of the chlorophosphite (10) were dissolved in 110 ml of dried toluene and cooled to 0° C. in an ice bath.

The 2,4-di-tert-butylphenol/toluene/Et$_3$N solution was added gradually to the chlorophosphite/toluene solution which had been cooled down to 0° C. beforehand.

On completion of addition, the mixture was warmed to room temperature gradually and while stirring overnight.

For workup, the amine hydrochloride obtained was filtered off. The residue obtained was washed with 30 ml of dried toluene. The mother liquor obtained was concentrated to dryness under reduced pressure.

Yield: 12.5 g

Chlorine content titration: 0.21/0.21% by weight

EXAMPLE 4

Synthesis of (VI)

To a solution of the chlorophosphite (10) (0.441 g; 0.367 mmol) in toluene (5 ml) is added dropwise at 0° C. while stirring a solution of 2-phenylphenol (0.5 g; 2.938 mmol) in a mixture of toluene (7 ml) and triethylamine (3.7 ml). The mixture is left to stir at room temperature overnight and filtered, the filtrate is concentrated under reduced pressure and the residue obtained is dried at 50° C./0.1 mbar for 2 h.

Purification by column chromatography (dichloromethane, R$_f$=0.82) gives 0.541 g (0.239 mmol; 65%) of the tetraphosphite (VI).

Analysis (calc. for C$_{146}$H$_{134}$O$_{16}$P$_4$=2268.54 g/mol): C, 77.34 (77.30) %; H, 5.98 (5.96) %; P, 5.85 (5.46) %.

$^{31}$P-NMR (CD$_2$Cl$_2$): 129.9 (s) ppm. $^1$H-NMR (CD$_2$Cl$_2$): 1.16 (36 H); 1.85 (6 H); 3.06 (4 H); 3.89 (4 H), 6.76 . . . 7.44 (84 H) ppm.

ESI-TOF HRMS: m/e 2290.8538 (M+Na)$^+$.

EXAMPLE 5

Synthesis of (VII)

To a solution of the chlorophosphite (10) (0.612 g; 0.511 mmol) in toluene (5 ml) is added dropwise at 0° C. while stirring a solution of 1-naphthol (0.589 g; 4.084 mmol) in a mixture of toluene (12 ml) and triethylamine (5.2 ml). The mixture is left to stir at room temperature overnight and filtered, the filtrate is concentrated under reduced pressure and the residue obtained is dried at 50° C./0.1 mbar for 2 h.

Purification by column chromatography (dichloromethane, $R_f$=0.77) gives 0.629 g (0.305 mmol; 60%) of the tetraphosphite (VII).

Analysis (calc. for $C_{130}H_{118}O_{16}P_4$=2060.24 g/mol): C, 75.67 (75.79) %; H, 5.99 (5.77) %; P, 6.01 (6.01) %.

$^{31}$P-NMR (CD$_2$Cl$_2$): 131.3 (s) ppm. $^1$H-NMR (CD$_2$Cl$_2$): 1.33 (36 H); 1.89 (6 H); 3.11 (4 H); 3.87 (4 H), 6.98 ... 8.19 (84 H) ppm.

ESI-TOF HRMS: m/e 2082.72565 (M+Na)$^+$.

EXAMPLE 6

Synthesis of (VIII)

To a solution of the chlorophosphite (10) (0.612 g; 0.511 mmol) in toluene (5 ml) is added dropwise at 0° C. while stirring a solution of 1-naphthol (0.589 g; 4.084 mmol) in a mixture of toluene (12 ml) and triethylamine (5.2 ml). The mixture is left to stir at room temperature overnight and filtered, the filtrate is concentrated under reduced pressure and the residue obtained is dried at 50° C./0.1 mbar for 2 h.

Purification by column chromatography (dichloromethane, $R_f$=0.82) gives 0.57 g (0.277 mmol; 54%) of the tetraphosphite (VIII).

Analysis (calc. for $C_{130}H_{118}O_{16}P_4$=2060.24 g/mol): C, 75.47 (75.79) %; H, 5.50 (5.77) %; P, 6.23 (6.01) %.

$^{31}$P-NMR (CD$_2$Cl$_2$): 129.5 (s) ppm. $^1$H-NMR (CD$_2$Cl$_2$): 1.34 (36 H); 1.90 (6 H); 3.13 (4 H); 3.89 (4 H), 7.05 ... 7.87 (84 H) ppm.

ESI-TOF HRMS: m/e 2082.72637 (M+Na)$^+$.

EXAMPLE 7

Synthesis of (IX)

To a solution of the chlorophosphite (10) (0.734 g; 0.613 mmol) in toluene (6 ml) is added dropwise at 0° C. while stirring a solution of methyl 4-hydroxybenzoate (0.746 g; 4.901 mmol) in a mixture of toluene (14 ml) and triethylamine (6.2 ml). The mixture is left to stir at room temperature overnight and filtered, and the filtrate is concentrated under reduced pressure.

The residue obtained is first dried at 50° C./0.1 mbar for 2 h and then taken up in dry boiling acetonitrile (10 ml). Storage of the solution at −23° C. gives 0.847 g (0.399 mmol; 65%) of the tetraphosphite (IX).

Analysis (calc. for $C_{114}H_{118}O_{32}P_4$=2124.05 g/mol): C, 64.50 (64.46) %; H, 5.50 (5.60) %; P, 5.85 (5.83) %.

$^{31}$P-NMR (CD$_2$Cl$_2$): 128.4 (s) ppm. $^1$H-NMR (CD$_2$Cl$_2$): 1.29 (36 H); 1.88 (6 H); 3.13 (4 H); 3.89 (4 H), 3.91 (24 H); 6.87 ... 8.06 (44 H) ppm.

ESI-TOF HRMS: m/e 2146.64606 (M+Na)$^+$.

EXAMPLE 8

Synthesis of (X)

To a solution of the chlorophosphite (10) (0.573 g; 0.478 mmol) in toluene (4 ml) is added dropwise at 0° C. while stirring a solution of 2,6-diphenylphenol (0.942 g; 3.826 mmol) in a mixture of toluene (12 ml) and triethylamine (5.9 ml). The mixture is stirred first at room temperature overnight, then at 70° C. for 4 h and at bath temperature 100° C. for another 2 h. The mixture is filtered and the filtrate is concentrated under reduced pressure. The residue obtained is dried at 50° C./0.1 mbar for 2 h.

Purification by column chromatography (hexane/dichloromethane (1:1), $R_f$=0.16) gives 0.392 g (0.136 mmol; 28%) of the tetraphosphite (X).

Analysis (calc. for $C_{194}H_{166}O_{16}P_4$=2877.32 g/mol): C, 80.81 (80.98) %; H, 5.92 (5.81) %; P, 4.19 (4.31) %.

$^{31}$P-NMR (CD$_2$Cl$_2$): 142.4 (s) ppm. $^1$H-NMR (CD$_2$Cl$_2$): 1.05 (36 H); 1.82 (6 H); 3.04 (4 H); 4.04 (4 H); 5.79 ... 7.64 (116 H) ppm.

ESI-TOF HRMS: m/e 2900.11232 (M+Na)$^+$.

EXAMPLE 9

Synthesis of (XI)

To a stirred solution of 2-chloro-4,4,5,5-tetraphenyl-1,3,2-dioxaphospholane (1.074 g; 2.493 mmol) in THF (6 ml) is added dropwise at 0° C. a solution of Hostanox 03 (ethylenebis[3,3-bis(3-tert-butyl-4-hydroxyphenyl)butyrate]) (0.451 g; 0.567 mmol) in triethylamine (0.71 ml) and THF (7 ml). The mixture is stirred first at room temperature overnight, then at 70° C. for 10 h, and filtered, and the filtrate is concentrated under reduced pressure. The residue obtained is dried at 50° C./0.1 mbar for 2 h and then crystallized from acetonitrile.

Yield: 0.66 g (0.278 mmol; 49%) of 92% product (assessment: P NMR).

$^{31}$P-NMR (CD$_2$Cl$_2$): 138.5 (s) ppm. $^1$H-NMR (CD$_2$Cl$_2$): 1.20 (36 H); 1.90 (6 H); 3.15 (4 H); 3.91 (4 H); 6.92 ... 7.63 (92 H) ppm.

ESI-TOF HRMS: m/e 2393.91863 (M+Na)$^+$.

EXAMPLE 10

Synthesis of (XII)

To a stirred solution of R-4-chlorodinaphtho[2,1-d:1',2'-f][1,3,2]dioxaphosphepine (1.143 g; 3.259 mmol) in THF (8 ml) is added dropwise at 0° C. a solution of Hostanox 03 (ethylenebis[3,3-bis(3-tert-butyl-4-hydroxyphenyl)butyrate]) (0.589 g; 0.741 mmol) in triethylamine (0.93 ml) and THF (9 ml). The mixture is stirred at room temperature overnight and filtered, and the filtrate is concentrated under reduced pressure. The residue obtained is dried at 50° C./0.1 mbar for 2 h. Purification by column chromatography (dichloromethane, $R_f$=0.71) gives 1.128 g (0.550 mmol; 74%) of the tetraphosphite (XII).

Analysis (calc. for $C_{130}H_{110}O_{16}P_4$=2052.15 g/mol): C, 75.90 (76.09) %; H, 5.56 (5.40) %; P, 6.14 (6.04) %.

$^{31}$P-NMR (CD$_2$Cl$_2$): 145.6 (s) ppm. $^1$H-NMR (CD$_2$Cl$_2$): 1.34 (36 H); 1.91 (6 H); 3.16 (4 H); 3.93 (4 H); 7.07 ... 8.08 (60 H) ppm.

EXAMPLE 11

Synthesis of (XIII)

To a solution of the chlorophosphite (10) (1.121 g; 0.936 mmol) in toluene (7 ml) is added dropwise at 0° C. while stirring a solution of 2-hydroxynicotinic acid (0.506 g; 3.742 mmol) in a mixture of toluene (13 ml) and triethylamine (5.6 ml). The mixture is stirred at room temperature overnight and filtered, and the filtrate is concentrated under reduced pressure. The residue obtained is dried at 50° C./0.1 mbar for 2 h and is used as obtained.

Yield: 0.67 g (0.458 mmol; 49%).

Analysis (calc. for $C_{74}H_{74}N_4O_{20}P_4$=1463.30 g/mol): C, 60.92 (60.74) %; H, 5.02 (5.10) %; P, 8.57 (8.47) %.

$^{31}$P-NMR (CD$_2$Cl$_2$): 115.1 (s) ppm. $^1$H-NMR (CD$_2$Cl$_2$): 1.18 (36 H); 1.84 (6 H); 3.08 (4 H); 3.85 (4 H); 7.00 . . . 8.63 (24 H) ppm.

EXAMPLE 12

Synthesis of (XIV)

To a solution of the chlorophosphite (10) (1.356 g; 1.144 mmol) in toluene (9 ml) is added dropwise at 0° C. while stirring a mixture of 1,8-diaminonaphthalene (0.724 g; 4.577 mmol), toluene (18 ml) and triethylamine (7.1 ml). The mixture is stirred at room temperature overnight and filtered, and the filtrate is concentrated under reduced pressure. The residue obtained is dried at 50° C./0.1 mbar for 2 h and is used as obtained.

Yield: 0.500 g (0.325 mmol; 28%).

Analysis (calc. for C$_{90}$H$_{94}$N$_8$O$_8$P$_4$=1539.68 g/mol): C, 70.46 (70.21) %; H, 6.15 (6.15) %; P, 7.95 (8.05) %.

$^{31}$P-NMR (CD$_2$Cl$_2$): 82.2 (s) ppm. $^1$H-NMR (CD$_2$Cl$_2$): 1.04 (36 H); 1.82 (6 H); 3.08 (4 H); 3.65 (4 H); 5.72 (m, 8 H); 6.51 . . . 7.25 (36 H) ppm.

ESI-TOF HRMS: m/e 1577.57657 (M+Na)$^+$.

EXAMPLE 13

Synthesis of (XV)

To a solution of the chlorophosphite (10) (1.585 g; 1.323 mmol) in toluene (20 ml) is added dropwise at 0° C. while stirring a solution of N-benzylmethylamine (1.282 g; 10.581 mmol) in a mixture of toluene (17 ml) and triethylamine (13.4 ml). The mixture is stirred at room temperature overnight and filtered, and the filtrate is concentrated under reduced pressure. The residue obtained is dried at 50° C./0.1 mbar for 2 h and then stirred with diethyl ether (10 ml). Filtration and concentration of the filtrate under reduced pressure yield the product as a white solid.

Yield: 1.62 g (0.863 mmol; 65%).

Analysis (calc. for C$_{114}$H$_{142}$N$_8$O$_8$P$_4$=1876.29 g/mol): C, 72.83 (72.97) %; H, 7.65 (7.63) %; N, 6.08 (5.97) %; P, 6.76 (6.60) %.

$^{31}$P-NMR (CD$_2$Cl$_2$): 128.9 (s) ppm. $^1$H-NMR (CD$_2$Cl$_2$): 1.47 (36 H); 1.97 (6 H); 2.68 (d, $^3$J$_{HP}$=6.9 Hz; 24 H), 3.21 (4 H); 3.97 (4 H); 4.23 (dd, $^3$J$_{HP}$=8.5 Hz; $^2$J$_{HH}$=14.7 Hz; 8 H); 4.40 (dd, $^3$J$_{HP}$=8.5 Hz; $^2$J$_{HH}$=14.7 Hz; 8 H); 7.05 . . . 7.39 (52 H) ppm.

INVENTIVE EXAMPLE 14

Reduction of Chlorine Level in (V)

a) Removal of Chlorine by Means of Degassed Ethanol+1% Degassed Water+5% Degassed DMAB at 0° C.

For removal of chlorine, 50 ml of degassed ethanol and 2.5 ml of degassed N,N'-dimethylaminobutane were first added to 10 g of the crude ligand (V) having a starting chlorine value of 0.2% by weight while stirring, and the mixture was stirred for 1 h. Thereafter, 0.5 ml of degassed water was added, the mixture was cooled to 0° C. and the suspension was stirred for 2 h. Subsequently, the solids were filtered off, washed twice with 40 ml of cold degassed ethanol, and dried.

Yield: 8.2 g (82%)

Chlorine content titration: 230 mg/kg (ppm)

b) Chlorine Removal by Means of Degassed Ethanol+ Triethylamine at 0° C.

For removal of chlorine, 600 ml of degassed ethanol and 0.1 ml of triethylamine were first added to 28.5 g of the crude ligand (V) having a starting chlorine value of 0.2% by weight while stirring. The mixture was stirred for 3 h, then cooled to 0° C. by means of an ice bath and stirred for another 1 h. The solids were filtered off, washed with 50 ml of cooled degassed ethanol and dried.

Yield: 20.05 g=72%

Chlorine content (Wickbold): 100 mg/kg (ppm)

c) Chlorine Removal by Means of Degassed Ethanol+ Triethylamine at 0° C.

For removal of chlorine, 600 ml of degassed ethanol and 0.2 ml of triethylamine were first added to 28.5 g of the crude ligand (V) having a starting chlorine value of 0.2% by weight while stirring. The mixture was stirred for 3 h, then cooled to 0° C. by means of an ice bath and stirred for another 1 h. The solids were filtered off, washed with 50 ml of cooled degassed ethanol and dried.

Yield: 20.05 g=72%

Chlorine content (Wickbold): 80 mg/kg (ppm)

INVENTIVE EXAMPLE 15

Synthesis of (V) with Undried Toluene as Solvent and Subsequent Removal of Chlorine In a 500 ml Schlenk flask, 36.9 g (0.177 mol) of 2,4-di-tert-butylphenol were admixed with 300 ml of degassed undried toluene and 28 ml (0.202 mol) of triethylamine.

In a 2000 ml Schlenk flask, 28.9 g (0.022 mol) of the chlorophosphite (10) were admixed with 300 ml of degassed toluene and cooled to 0° C. in an ice bath.

The 2,4-di-tert-butylphenol/toluene/Et$_3$N solution was added gradually to the chlorophosphite/toluene solution which had been cooled down to 0° C. On completion of addition, the reaction mixture was brought to room temperature while stirring overnight.

The next morning, the mixture was heated to 40° C. with vigorous stirring for 30 min. The mixture was then stirred at 80° C. for a further 45 minutes.

After cooling to room temperature, the amine hydrochloride obtained was filtered off. The frit residue obtained was washed with 50 ml of degassed toluene. The mother liquor obtained was collected and concentrated to dryness under reduced pressure in a 2 ml Schlenk flask which had been repeatedly evacuated and filled with inert gas.

For further workup, the residue obtained was pulverized and dried overnight. After drying, 750 ml of degassed ethanol and 1.5 ml of triethylamine were added to the pulverized solid. The mixture was stirred at room temperature overnight and then cooled to 0° C. by means of an ice bath and stirred for another 2 h. The solids were filtered, washed with a little cooled degassed ethanol and dried.

Yield: 36.31 g (63%)

Chlorine content: Wickbold: 75 mg/kg (ppm)

COMPARATIVE EXAMPLE 16

Reduction of Chlorine Level in (V) with Pure Water

Alternative Preparation of Compound (V):

To 43.5 g (0.084 mol) of bis(2,4-di-tert-butylphenyl) phosphorochloridite weighed out in a 1000 ml Schlenk flask were added, while stirring, 180 ml of dried toluene. The solution is cooled to 0° C.

In a second 500 ml Schlenk flask, 15.1 g (0.019 mol) of Hostanox 03 (ethylenebis[3,3-bis(3-tert-4-hydroxyphenyl)butyrate]) were admixed with 210 ml of dried toluene and 24.78 ml=18 g (0.176 mol) of degassed triethylamine while stirring. This reactant mixture dissolved completely after about 5 minutes. A clear solution was obtained. The solution was subsequently added dropwise while stirring to the chlorophosphite solution which had been cooled to 0° C. The reaction mixture was stirred at room temperature overnight.

For workup, the amine hydrochloride obtained was filtered off, and the filtrate was concentrated to dryness under reduced pressure and subjected to thorough further drying.

Crude product result: The NMR spectrum shows about 98% P compound (V), and further minor secondary components.

Chlorine content: Titration 0.12/0.12% by weight (=1200/1200 mg/kg (ppm))

Comparative example of chlorine reduction: 10 g of the crude product were weighed out and stirred with 100 ml of degassed water (Chromasolv material) under argon for 30 minutes. Subsequently, the heterogeneous mixture was filtered off, rinsed through three times with 10 ml of water and dried overnight at.

Yield: 9 g (90%)

31P NMR: 88.8% P compound (V), 3.8% P phosphite 1, 0.2% P phosphite, 4.3% P phosphite, 2.4% P P—H oxide, 0.3% P phosphite Chlorine content: 0.11/0.11% by weight (=1100/1200 mg/kg (ppm))

The results are summarized once again in Table 1.

TABLE 1

Chlorine values of the organotetraphosphites purified in accordance with the invention

| | Solvent | Base* [%] | Water added* [%] | Yield [%] | Chlorine content [ppm] |
|---|---|---|---|---|---|
| 14a) | Ethanol | 5 | 1 | 82 | 230 |
| 14b) | Ethanol | 0.017 | — | 72 | 100 |
| 14c) | Ethanol | 0.033 | — | 72 | 80 |
| 15) | Ethanol | 0.2 | — | 63 | 75 |
| 16)** | Water | — | 100 | 90 | 1100 |

*Percentages relate to the solvent content
**Comparative example

The above examples show firstly that the process according to the invention can significantly reduce the chlorine content of organotetraphosphites, for example from a starting chlorine content of about 2000 ppm to a final content of <250 ppm or to a final content of ≤100 ppm.

As becomes clear from the comparative example (Example 16), the use of pure water as solvent does not lead to the desired result of reducing the chlorine level. Moreover, a comparison of the $^{31}$P NMR data from this experiment shows that, when pure water is used, about 10% more secondary components have formed as a result of partial hydrolysis.

The examples also show that the process according to the invention can also be conducted in the presence of traces of water (cf. Example 14a, in which it was possible to reduce the chlorine content to 230 ppm with a yield of 82%). It is therefore possible to use water-containing solvents in the process as well, and so drying thereof is not necessarily required. Water in the case of phosphites can lead to decompositions and hence to yield losses or to formation of secondary components, as shown by the comparative example. This is not observed here, in the case of use of water-containing solvents (cf. Table 1). This means that it is possible to dispense with an inconvenient and costly drying of the solvents. This makes an industrial scale synthesis more economically viable, since drying of the solvents beforehand is unnecessary and hence synthesis steps can be shortened.

The invention claimed is:

1. Process for reducing the chlorine content in an organotetraphosphite of one of the general formulae I and II:

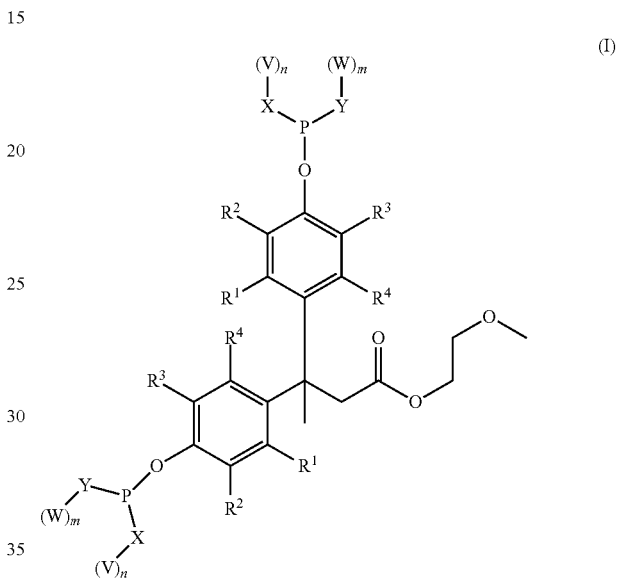

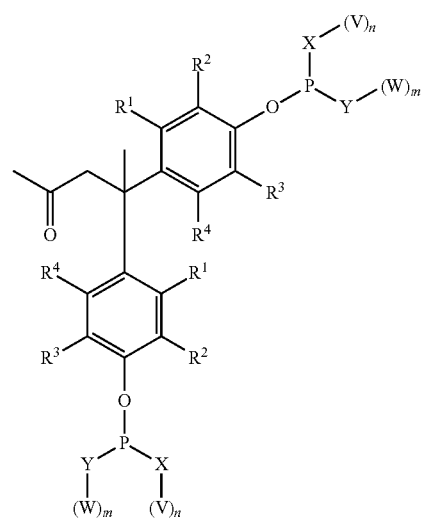

-continued (II)

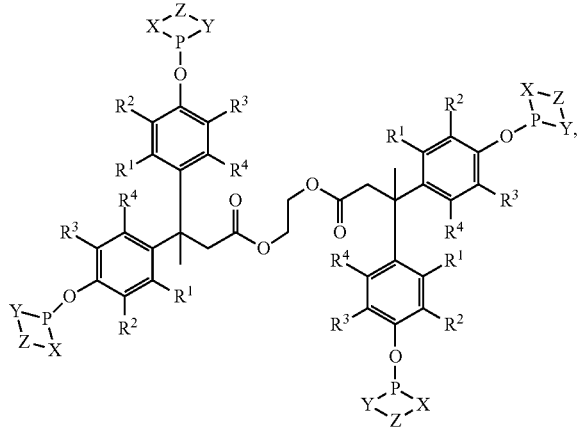

where
R$^1$, R$^2$, R$^3$, R$^4$ are each independently selected from: —H, —(C$_1$-C$_{12}$)-alkyl;
V and W are each independently selected from:
—H, —(C$_1$-C$_{12}$)-alkyl, —O—(C$_1$-C$_{12}$)-alkyl, —(C$_1$-C$_{12}$)-heteroalkyl, —(C$_4$-C$_{20}$)-aryl, —(C$_4$-C$_{20}$)-aryl-(C$_1$-C$_{12}$)-alkyl, —(C$_4$-C$_{20}$)-aryl-O—(C$_1$-C$_{12}$)-alkyl, —(C$_1$-C$_{12}$)-alkyl-(C$_4$-C$_{20}$)-aryl, —(C$_4$-C$_{20}$)-aryl-COO—(C$_1$-C$_{12}$)-alkyl, —(C$_4$-C$_{20}$)-aryl-CONH—(C$_1$-C$_{12}$)-alkyl, —(C$_4$-C$_{20}$)-aryl-CON[(C$_1$-C$_{12}$)-alkyl]$_2$, -(C$_4$-C$_{20}$-heteroaryl, —(C$_4$-C$_{20}$)-heteroaryl-(C$_1$-C$_{12}$)-alkyl, —(C$_3$-C$_{12}$)-cycloalkyl, —(C$_3$-C$_{12}$)-cycloalkyl-(C$_1$-C$_{12}$)-alkyl, —(C$_3$-C$_{12}$)-heterocycloalkyl, —(C$_3$-C$_{12}$)-heterocycloalkyl-(C$_1$-C$_{12}$)-alkyl, —CO—(C$_1$-C$_{12}$)-alkyl, —CO—(C$_4$-C$_{20}$)-aryl, —CO—(C$_4$-C$_{20}$)-heteroalkyl, —(C$_4$-C$_{20}$)-aryl-CO—(C$_1$-C$_{12}$)-alkyl, —(C$_4$-C$_{20}$)-aryl-CO—(C$_4$-C$_{20}$)-aryl;
X and Y are each independently selected from O and N;
where, in the case that X is O, n=1,
and, in the case that Y is O, m=1,
and, in the case that X is N, n=1 or 2,
and, in the case that Y is N, m=1 or 2;
Z is selected from:
—(C$_1$-C$_{14}$)-alkyl- , —(C$_4$-C$_{20}$)-aryl-, —(C$_4$-C$_{20}$)-aryl-(C$_1$-C$_{12}$)- alkyl-, —(C$_1$-C$_{14}$)-heteroalkyl-, —(C$_4$-C$_{20}$)-heteroaryl-, —CO—(C$_4$-C$_{14}$)-heteroaryl-, —CO—(C$_4$-C$_{20}$)-aryl-, —(C$_3$-C$_{12}$)-cycloalkyl-, —(C$_3$-C$_{12}$)-heterocycloalkyl-, —(C$_4$-C$_{20}$)-aryl-CO—(C$_4$-C$_{20}$)-aryl-, —(C$_1$-C$_{14}$)-alkyl-O—(C$_1$-C$_{14}$)-alkyl-;
where the alkyl, heteroalkyl, cycloalkyl, heterocycloalkyl, aryl and heteroaryl groups mentioned are optionally mono- or polysubstituted;
comprising the following process steps:
a) contacting the organotetraphosphite with a solution comprising at least one solvent and at least one base, where the at least one solvent is selected from aromatics, alcohols, acetone, ethyl acetate, acetonitrile and ethers, and where the at least one base is selected from amine bases, alkoxides, pyridine, pyridine derivatives, N-methyl-2-pyrrolidone, triethylamine and triethanolamine,
b) adjusting the temperature to a value in the range from −20° C. to +15° C.,
c) removing the purified organotetraphosphite.

2. Process according to claim 1,
wherein the at least one solvent is selected from acetonitrile, ethyl acetate, ethanol, propanol, toluene.
3. Process according to claim 1,
wherein the solution with which the organotetraphosphite is contacted in step a) contains, as well as the at least one solvent and the at least one base, also max. 5% water based on the solvent content.
4. Process according to claim 1,
wherein the at least one base is selected from triethylamine and dimethylaininobutane.
5. Process according to claim 1,
where X and Y are O.
6. Process according to claim 1,
where X and Y are N.
7. Process according to claim 1,
where V and W are each independently selected from:
—H, —(C$_1$-C$_{12}$)-alkyl, —O—(C$_1$-C$_{12}$)-alkyl, —(C$_4$-C$_{20}$)-aryl, —(C$_4$-C$_{20}$)-aryl-(C$_1$-C$_{12}$)-alkyl, —(C$_4$-C$_{20}$)-aryl-O—(C$_1$-C$_{12}$)-alkyl, —(C$_1$-C$_{12}$)-alkyl-(C$_4$-C$_{20}$)-aryl, —(C$_4$-C$_{20}$)-aryl-COO—(C$_1$-C$_{12}$)-alkyl.
8. Process according to claim 1,
where V and W are, or just one of the substituents V and W is,

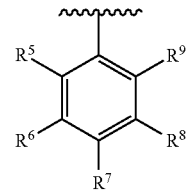

where R$^5$, R$^6$, R$^7$, R$^8$, R$^9$ are independently selected from
—H, —(C$_1$-C$_{12}$)-alkyl,
—O—(C$_1$-C$_{12}$)-alkyl, -phenyl, —COO—(C$_1$-C$_{12}$)-alkyl.
9. Process according to claim 1,
where Z is selected from:

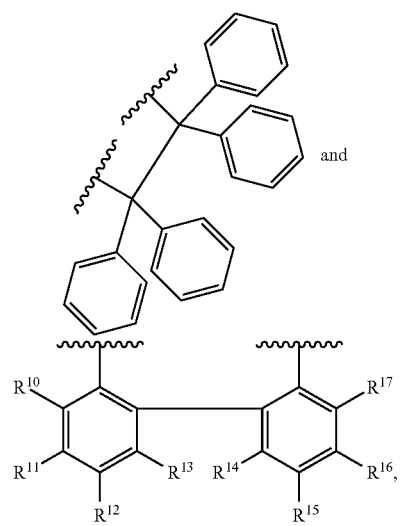

where R$^{10}$, R$^{11}$, R$^{12}$, R$^{13}$, R$^{14}$, R$^{15}$, R$^{16}$, R$^{17}$ are each independently selected from:
—H, —(C$_1$-C$_{12}$)-alkyl, —O—(C$_1$-C$_{12}$)-alkyl, —O—(C$_6$-C$_{20}$)-aryl, —(C$_6$-C$_{20}$)-aryl, -halogen (such as Cl, F, Br, I), COO—(C$_1$-C$_{12}$)-alkyl, CONH—(C$_1$-C$_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$.

10. Process according to claim 1, wherein the organotetraphosphite used in process step a) has a chlorine content of 1500 ppm to 100 000 ppm.

11. Process according to claim 1, wherein the purified organotetraphosphite has a chlorine content of <1000 ppm.

12. Process according to claim 1, where $R^1$, $R^3$, $R^4$ are —H.

13. Process according to claim 1, where $R^2$ is tert-butyl.

14. Process according to claim 1, where the organotetraphosphite has one of the structural formulae III, IV, V, VI, VII, VIII, IX, X, XI, XII, XIII, XIV and XV:

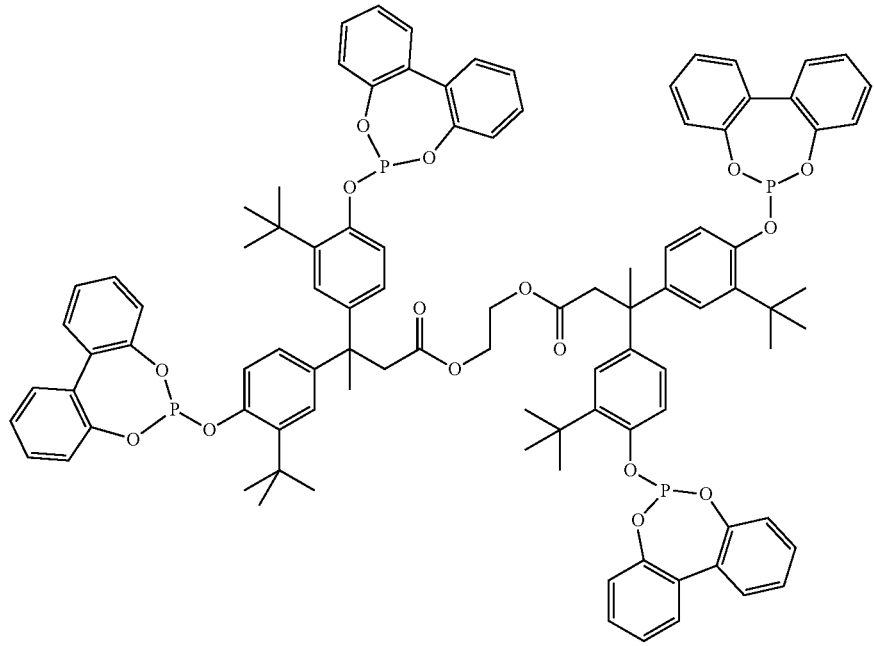

(III)

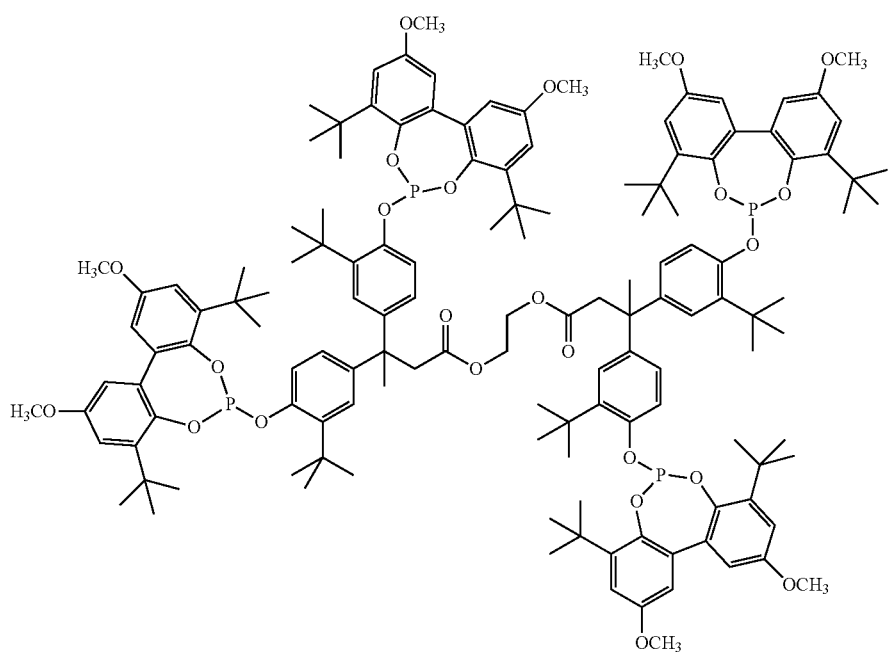

(IV)

(V)
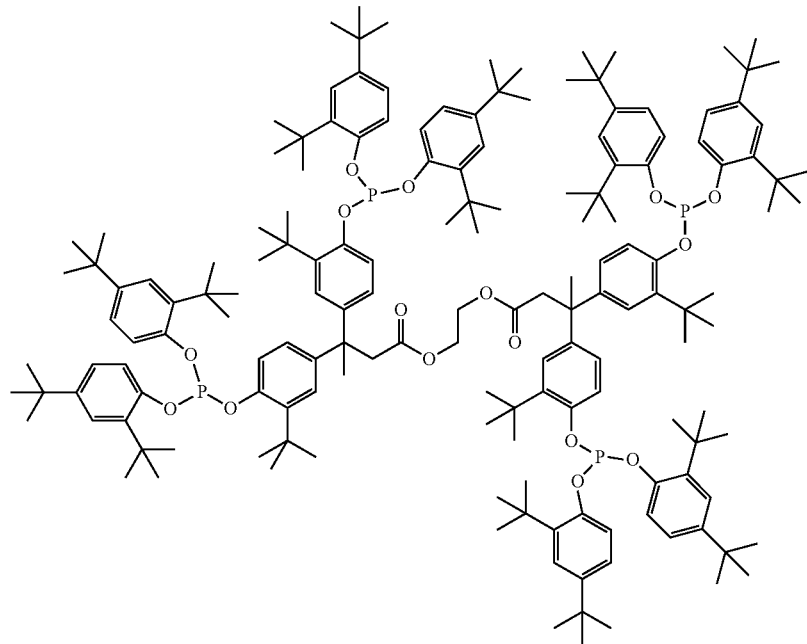
(VI)
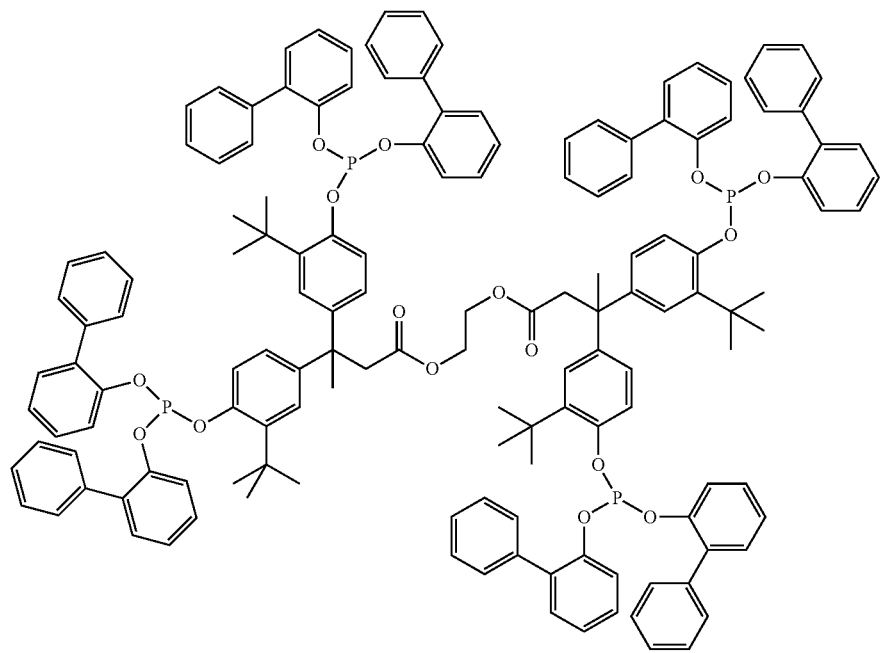

(VII)
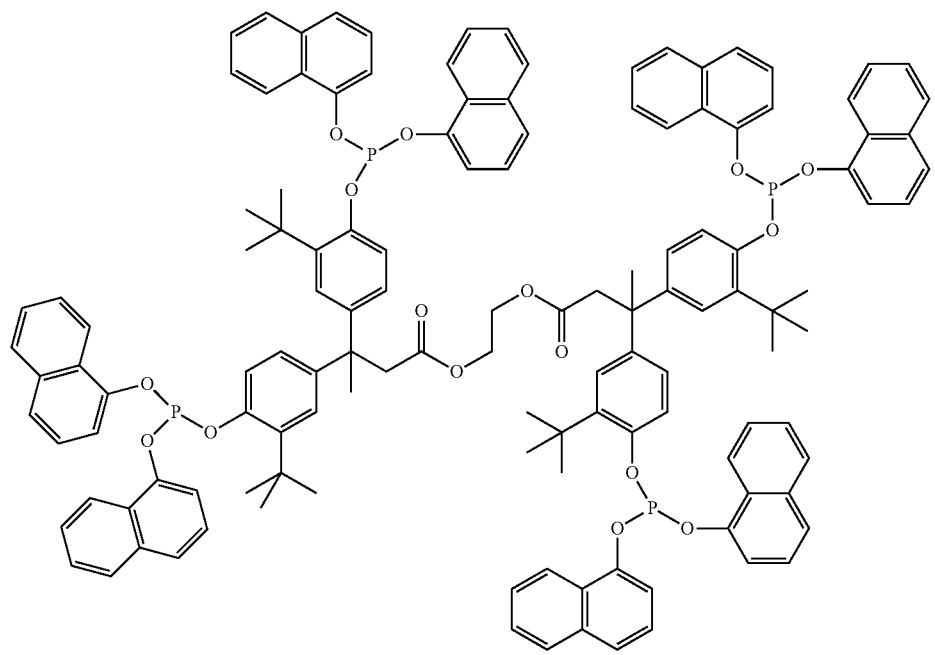
(VIII)
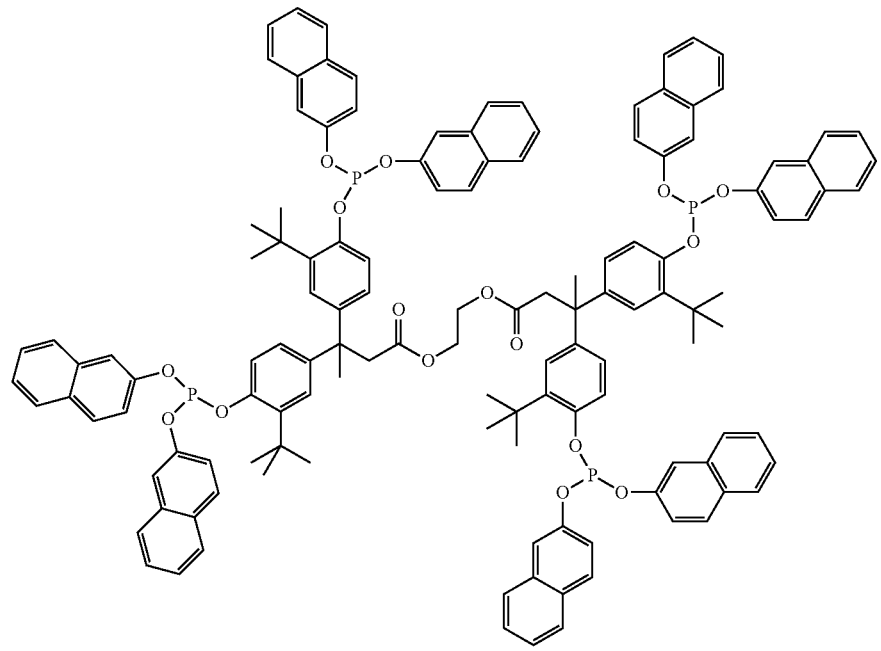

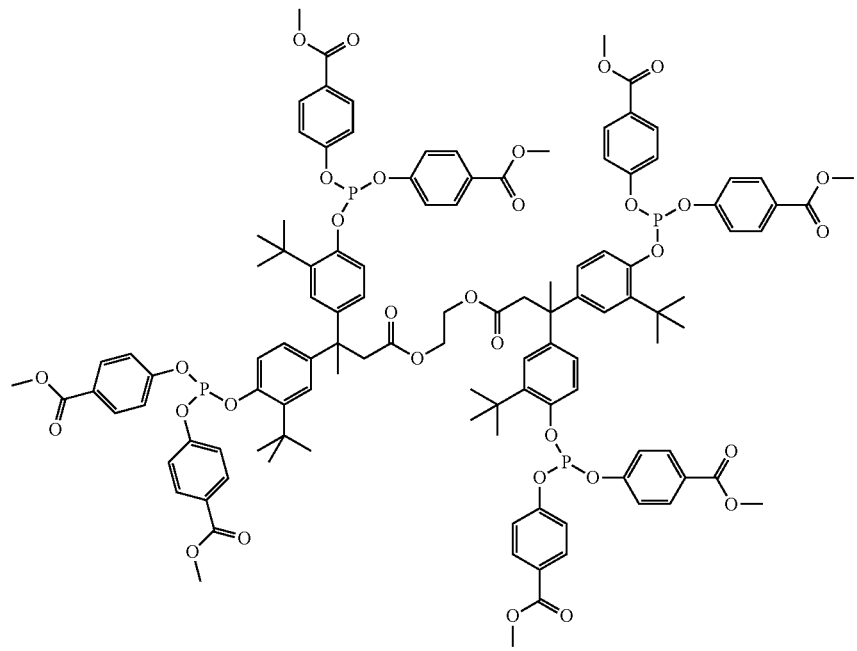
(IX)
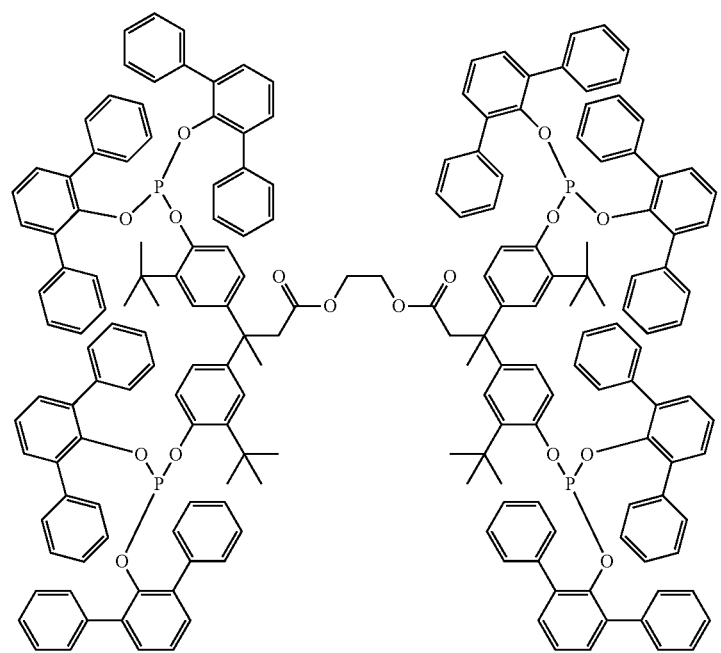
(X)

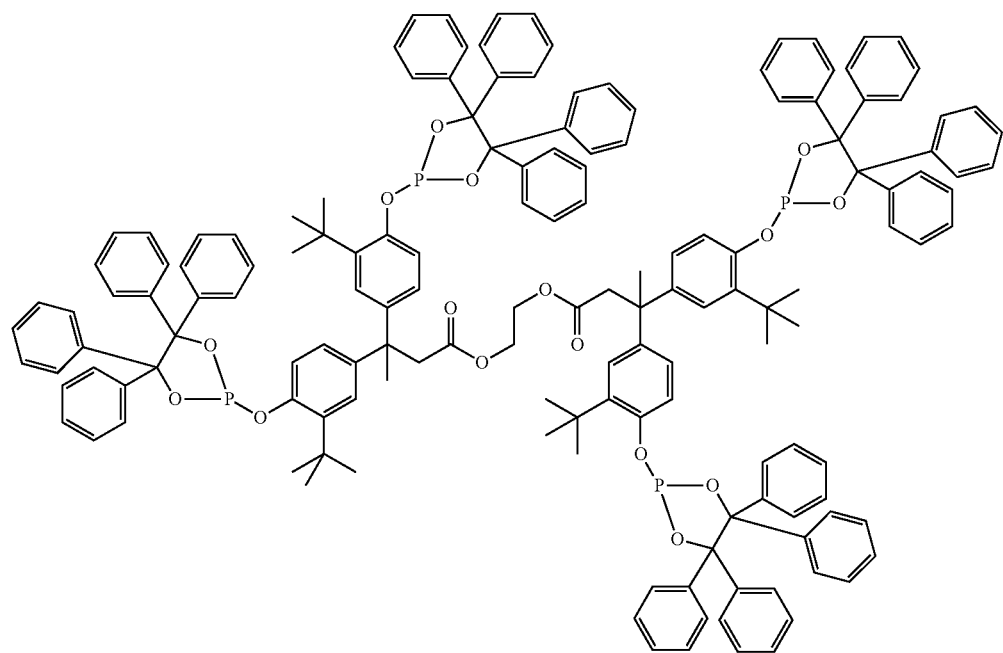
(XI)
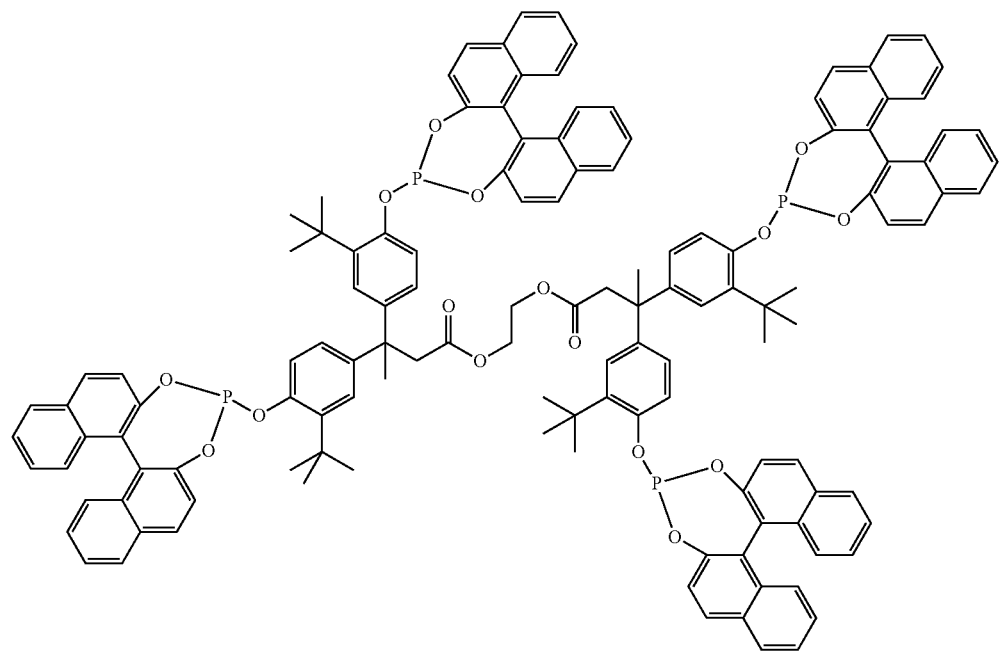
(XII)

(XIII)
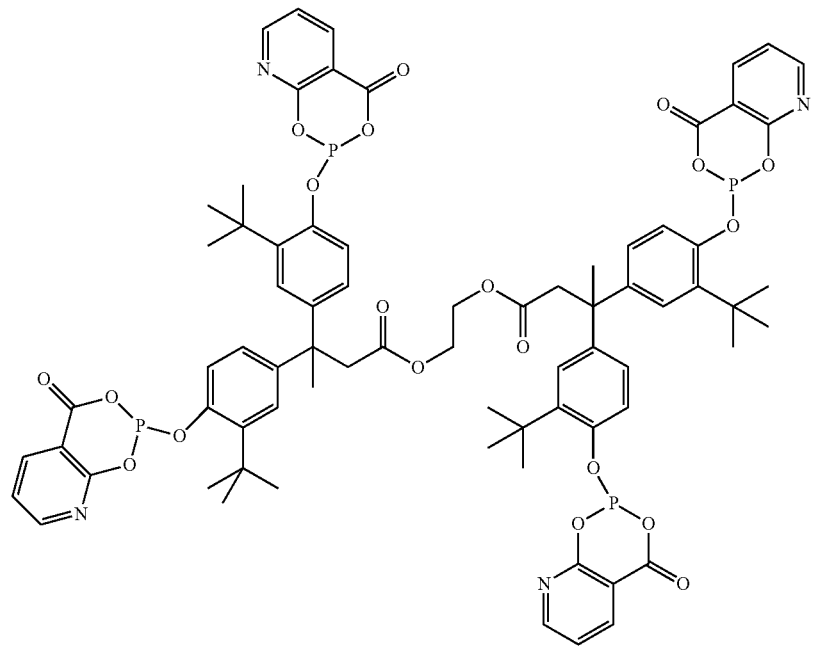
(XIV)
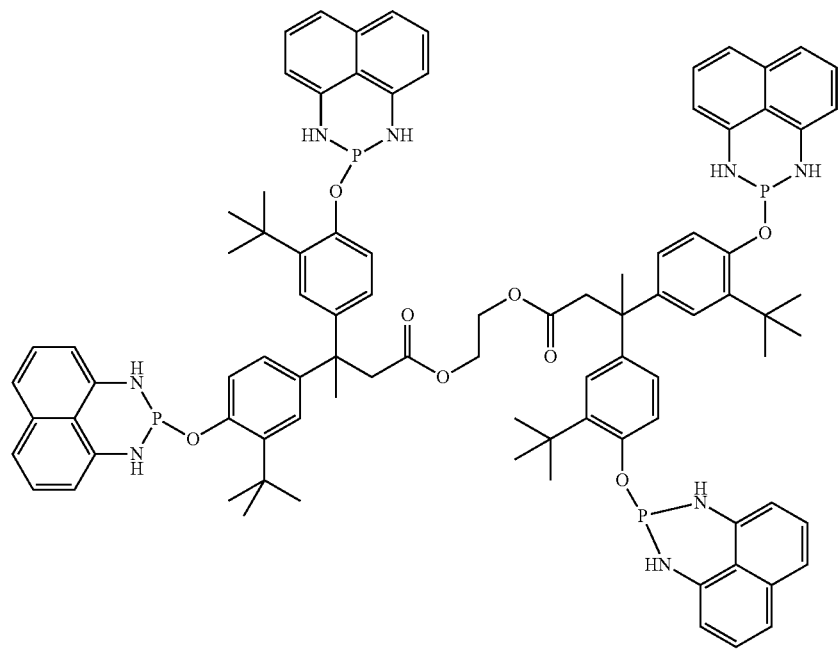

-continued
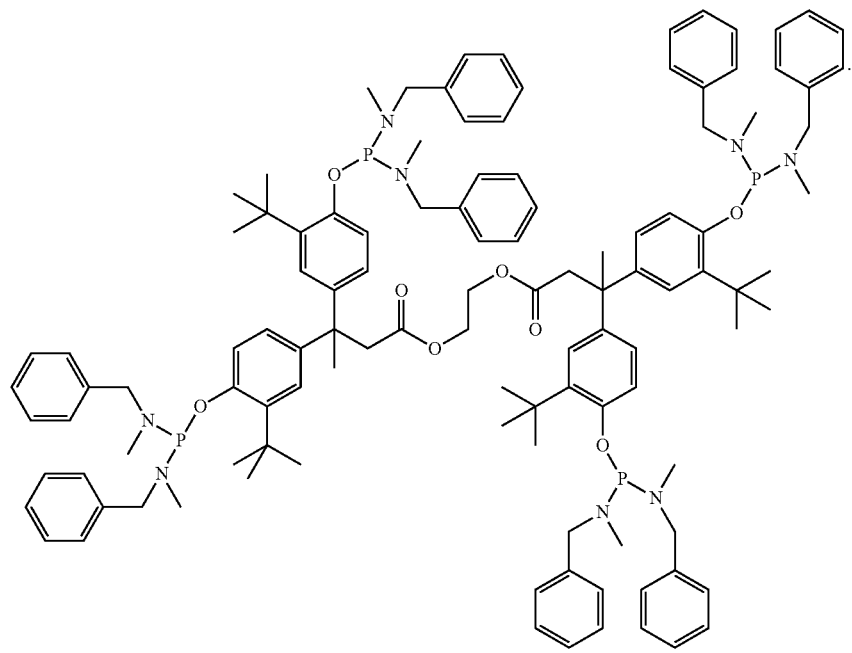
(XV)
* * * * *